United States Patent
Hawiger et al.

(10) Patent No.: US 11,026,992 B2
(45) Date of Patent: *Jun. 8, 2021

(54) COMPOSITIONS AND METHODS FOR PREVENTING AND REDUCING INFLAMMATION AND TREATING DISORDERS ASSOCIATED WITH INFLAMMATION

(71) Applicant: Vanderbilt University, Nashville, TN (US)

(72) Inventors: Jack J. Hawiger, Nashville, TN (US); Ruth Ann Veach, Brentwood, TN (US); Yan Liu, Nashville, TN (US); Huan Qiao, Nashville, TN (US); Lukasz S. Wylezinski, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/448,960

(22) Filed: Jun. 21, 2019

(65) Prior Publication Data

US 2020/0046799 A1 Feb. 13, 2020

Related U.S. Application Data

(63) Continuation of application No. 15/055,915, filed on Feb. 29, 2016, now Pat. No. 10,342,847.

(60) Provisional application No. 62/121,685, filed on Feb. 27, 2015.

(51) Int. Cl.
*A61K 38/10* (2006.01)
*A61K 38/18* (2006.01)
*C07K 7/00* (2006.01)

(52) U.S. Cl.
CPC .......... *A61K 38/10* (2013.01); *A61K 38/1825* (2013.01); *C07K 7/00* (2013.01); *C07K 2319/00* (2013.01)

(58) Field of Classification Search
CPC ................ A61K 38/10; A61K 38/1825; C07K 2319/00; C07K 7/00
See application file for complete search history.

(56) References Cited

U.S. PATENT DOCUMENTS

| | | | |
|---|---|---|---|
| 6,495,322 B1 | 12/2002 | Ni et al. | |
| 8,324,148 B2 | 12/2012 | Hawiger et al. | |
| 8,420,096 B2 | 4/2013 | Hawiger et al. | |
| 2012/0058137 A1 | 3/2012 | Bonny | |

OTHER PUBLICATIONS

Waki Hosoda, BCL10 as a useful marker for pancreatic acinar cell carcinoma, especially using endoscopic ultrasound cytology specimens, Pathology Internation, vol. 63, Issue3, Mar. 2013 pp. 176-182.*

Bhattacharyya, S., Borthakur, A., Pant, N., Dudeja, P. K., & Tobacman, J. K. (2007). Bcl10 mediates LPS-induced activation of NF-κB and IL-8 in human intestinal epithelial cells. American Journal of Physiology—Gastrointestinal and Liver Physiology, 293(2), G429-G437.

Bhattacharyya, S., Gill, R., Chen, M. L., Zhang, F., Linhardt, R. J., Dudeja, P. K., & Tobacman, J. K. (2008). Toll-like receptor 4 mediates induction of the Bcl10-NFκB-interleukin-8 inflammatory pathway by carrageenan in human intestinal epithelial cells. Journal of Biological Chemistry, 283(16), 10550-10558.

Blonska, M., & Lin, X. (2009). CARMA1-mediated NF-κB and JNK activation in lymphocytes. Immunological reviews, 228(1), 199-211.

Colgan, O. C. et al. (2007). Regulation of bovine brain microvascular endothelial tight junction assembly and barrier function by laminar shear stress. American Journal of Physiology-Heart and Circulatory Physiology, 292(6), H3190-H3197.

Delekta, P. C., Apel, I. J., Gu, S., Siu, K., Hattori, Y., McAllister-Lucas, L. M., & Lucas, P. C. (2010). Thrombin-dependent NF-κb activation and monocyte/endothelial adhesion are mediated by the CARMA3• Bcl10• MALT1 signalosome. Journal of Biological Chemistry, 285(53), 41432-41442.

Desai, T. R., Leeper, N. J., Hynes, K. L., & Gewertz, B. L. (2002). Interleukin-6 causes endothelial barrier dysfunction via the protein kinase C pathway. Journal of surgical research, 104(2), 118-123.

DiGiandomenico, A., Wylezinski, L. S., & Hawiger, J. (2009). Intracellular delivery of a cell-penetrating SOCS1 that targets IFN-γ signaling. Science signaling, 2(80), ra37.

Fletcher, T. C., DiGiandomenico, A., & Hawiger, J. (2010). Extended anti-inflammatory action of a degradation-resistant mutant of cell-penetrating suppressor of cytokine signaling 3. Journal of Biological Chemistry, 285(24), 18727-18736.

Friesel, R., & Maciag, T. (1988). Internalization and degradation of heparin binding growth factor-I by endothelial cells. Biochemical and biophysical research communications, 151(3), 957-964.

Hawiger, J. (1999). Noninvasive intracellular delivery of functional peptides and proteins. Current opinion in chemical biology, 3(1), 89-94.

Hawiger, J., Veach, R. A., & Zienkiewicz, J. (2015). New paradigms in sepsis: from prevention to protection of failing microcirculation. Journal of Thrombosis and Haemostasis, 13(10), 1743-1756.

(Continued)

Primary Examiner — James H Alstrum-Acevedo
Assistant Examiner — Erinne R Dabkowski
(74) Attorney, Agent, or Firm — Meunier Carlin & Curfman LLC

(57) ABSTRACT

The present invention relates to compositions and methods for preventing and reducing inflammation and preventing and treating diseases and disorders associated with inflammation. It has been shown that CRADD plays a pivotal role in maintaining the integrity of endothelial monolayers. The recombinant cell-penetrating CRADD protein (CP-CRADD)-based compositions and methods described herein provide for the development of a novel treatment for inflammatory vascular disorders including cardiovascular, cerebrovascular, respiratory, gastrointestinal, and renal systems.

13 Claims, 8 Drawing Sheets

Specification includes a Sequence Listing.

(56) References Cited

OTHER PUBLICATIONS

Imler, J. L., & Zheng, L. (2004). Biology of Toll receptors: lessons from insects and mammals. Journal of leukocyte biology, 75(1), 18-26.

Jo, D., Liu, D., Yao, S., Collins, R. D., & Hawiger, J. (2005). Intracellular protein therapy with SOCS3 inhibits inflammation and apoptosis. Nature medicine, 11(8), 892-898.

Kenne, E., & Lindbom, L. (2011). Imaging inflammatory plasma leakage in vivo. Thrombosis and haemostasis, 105(5), 783.

Lin, Q., Liu, Y., Moore, D. J., Elizer, S. K., Veach, R. A., Hawiger, J., & Ruley, H. E. (2012). Cutting edge: the "death" adaptor CRADD/RAIDD targets BCL10 and suppresses agonist-induced cytokine expression in T lymphocytes. The Journal of Immunology, 188(6), 2493-2497.

Londoño, D., Carvajal, J., Strle, K., Kim, K. S., & Cadavid, D. (2011). IL-10 Prevents apoptosis of brain endothelium during bacteremia. The Journal of Immunology, 186(12), 7176-7186.

Martin, D., Galisteo, R., & Gutkind, J. S. (2009). CXCL8/IL8 stimulates vascular endothelial growth factor (VEGF) expression and the autocrine activation of VEGFR2 in endothelial cells by activating NFκB through the CBM (Carma3/Bcl10/Malt1) complex. Journal of Biological Chemistry, 284(10), 6038-6042.

McAllister-Lucas, L. M., Jin, X., Gu, S., Siu, K., McDonnell, S., Ruland, J., . . . & Lucas, P. C. (2010). The CARMA3-Bcl10-MALT1 signalosome promotes angiotensin II-dependent vascular inflammation and atherogenesis. Journal of Biological Chemistry, 285(34), 25880-25884.

Paul, S., & Schaefer, B. C. (2013). A new look at T cell receptor signaling to nuclear factor-κB. Trends in immunology, 34(6), 269-281.

Qiao, H., & May, J. M. (2012). Interaction of the transcription start site core region and transcription factor YY1 determine ascorbate transporter SVCT2 exon 1a promoter activity. PloS one, 7(4), e35746.

Rawlings, D. J., Sommer, K., & Moreno-García, M. E. (2006). The CARMA1 signalosome links the signalling machinery of adaptive and innate immunity in lymphocytes. Nature Reviews Immunology, 6(11), 799-812.

Rueda, D. et al. (2007). Bcl10 controls TCR-and FcγR-induced actin polymerization. The Journal of Immunology, 178(7), 4373-4384.

Satta, N., Kruithof, E. K., Reber, G., & De Moerloose, P. (2008). Induction of TLR2 expression by inflammatory stimuli is required for endothelial cell responses to lipopeptides. Molecular immunology, 46(1), 145-157.

Stamatovic, S. M., Keep, R. F., Kunkel, S. L., & Andjelkovic, A. V. (2003). Potential role of MCP-1 in endothelial cell tight junctionopening': signaling via Rho and Rho kinase. Journal of cell science, 116(22), 4615-4628.

Tiscornia, G., Singer, O., & Verma, I. M. (2006). Production and purification of lentiviral vectors. Nature Protocols-Electronic Edition-, 1(1), 241.

Veach, R. A., Liu, D., Yao, S., Chen, Y., Liu, X. Y., Downs, S., & Hawiger, J. (2004). Receptor/transporter-independent targeting of functional peptides across the plasma membrane. Journal of Biological Chemistry, 279(12), 11425-11431.

* cited by examiner

FIG 1A
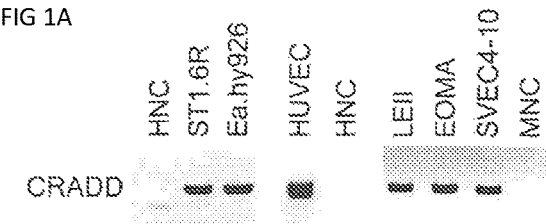
FIG 1C
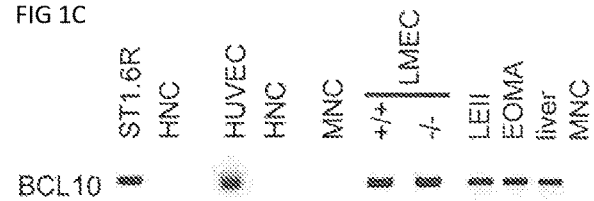
FIG 1B
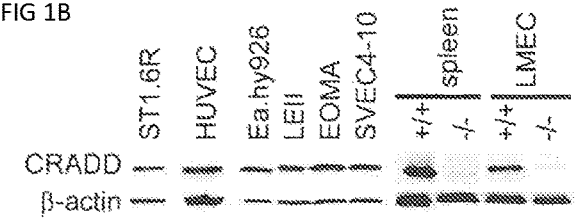
FIG 1D IP: IRAK1
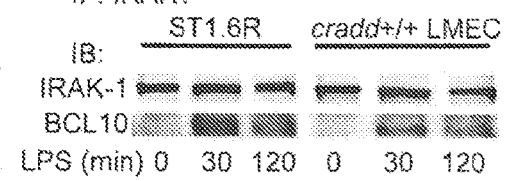

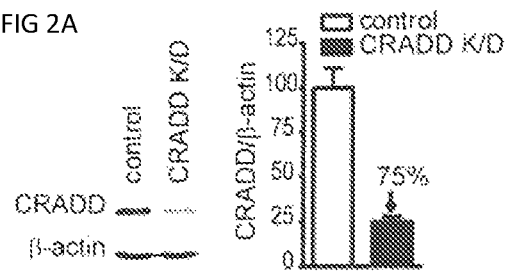
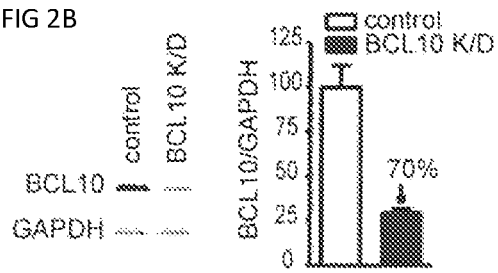
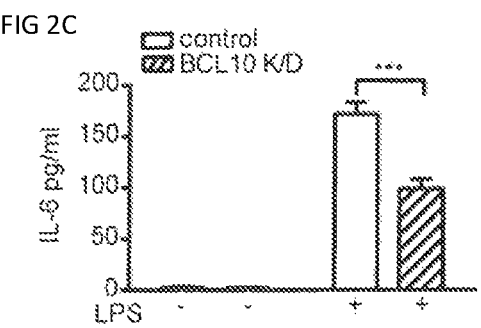
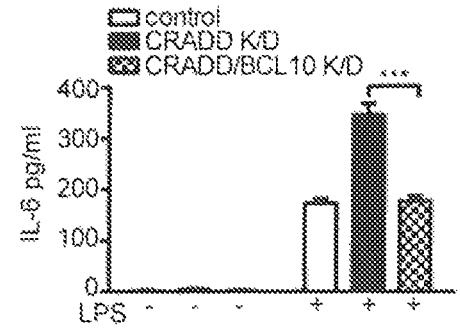
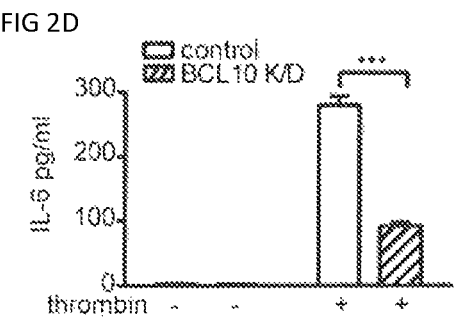
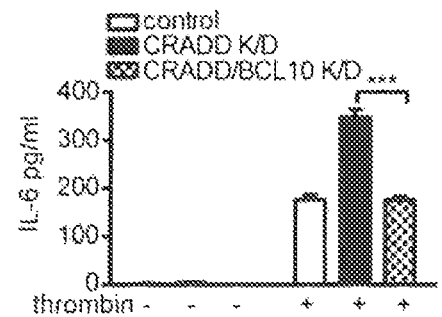
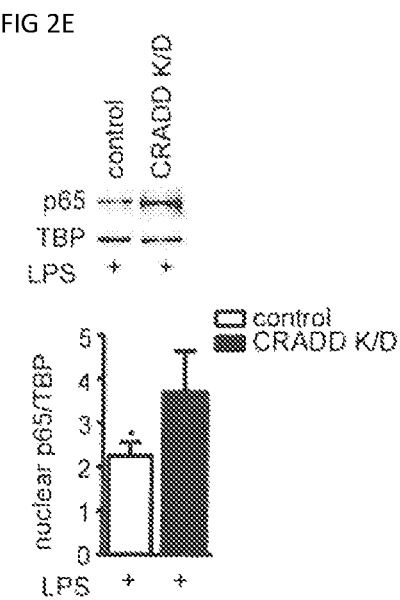
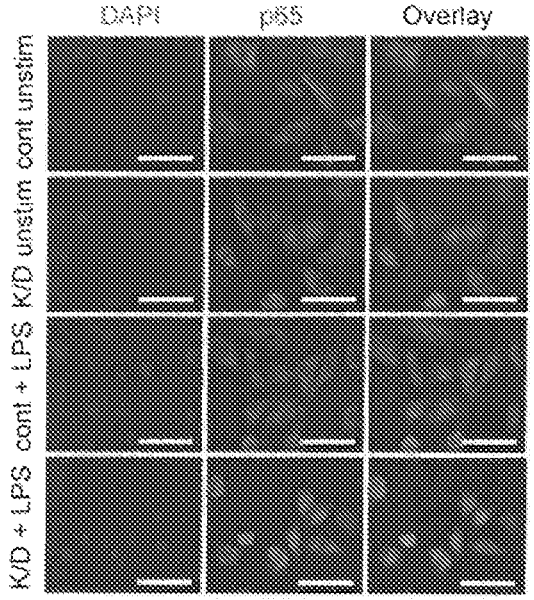

stained gel

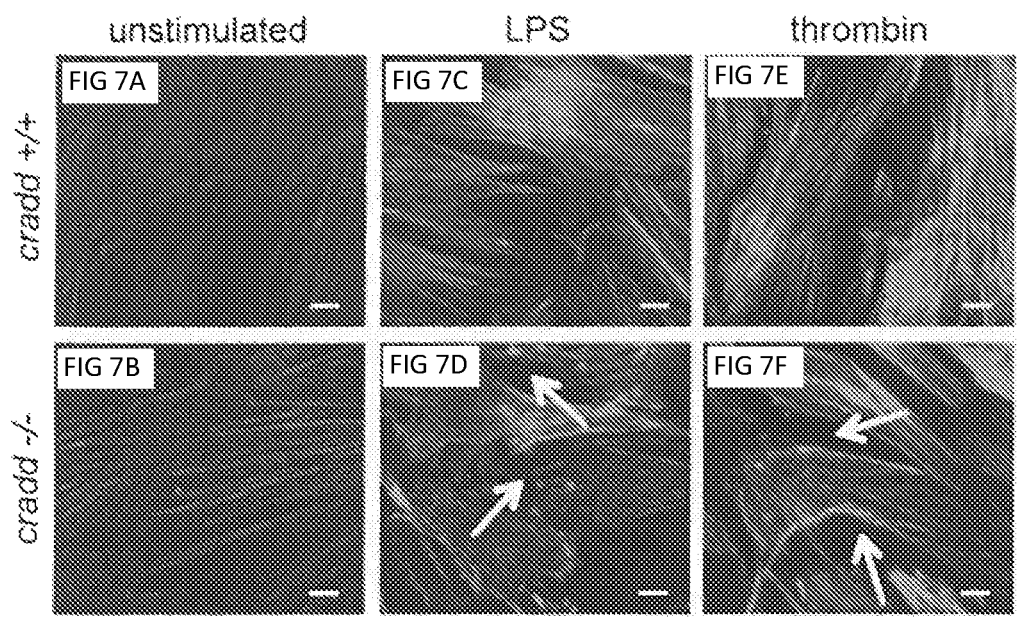

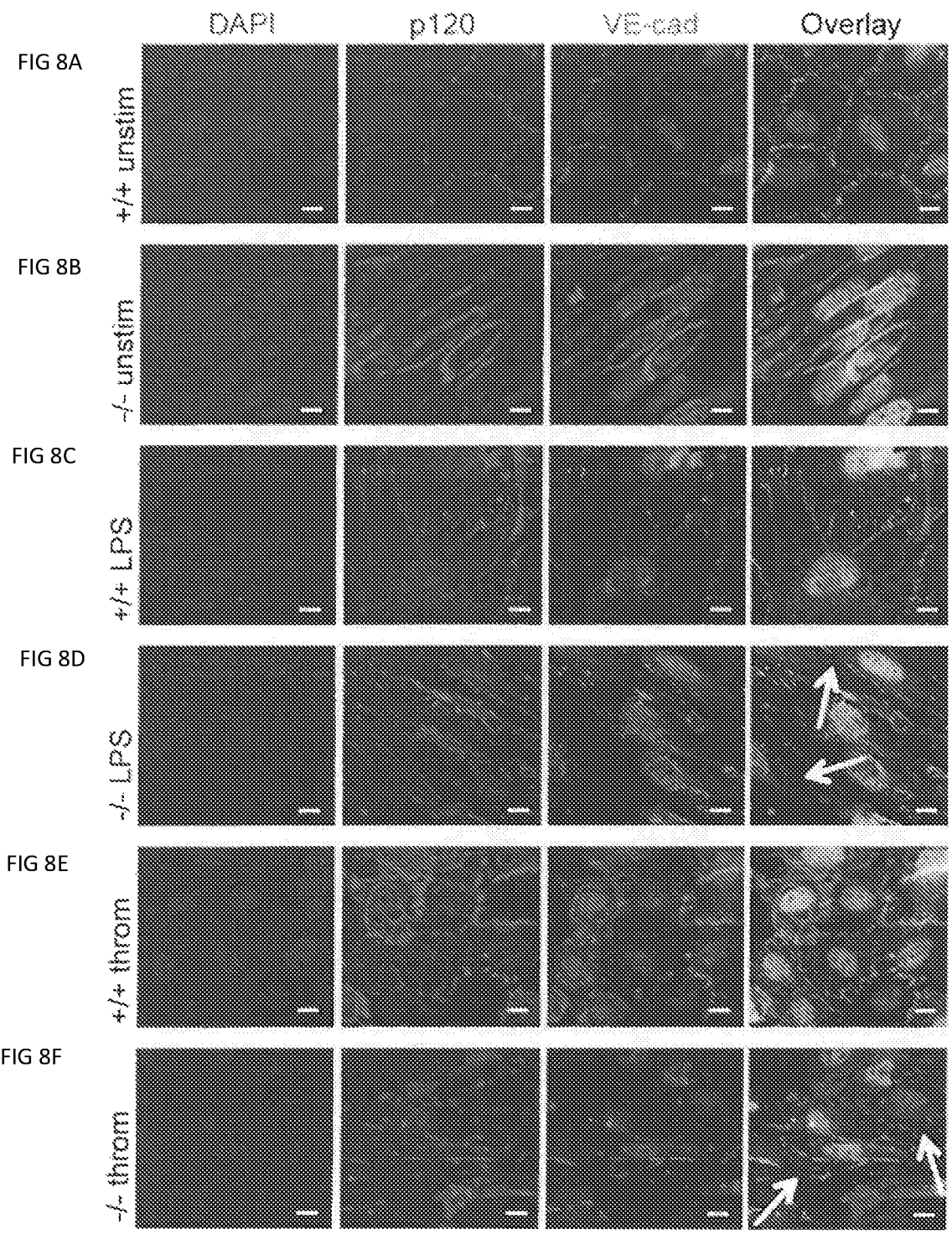

SEQUENCE LISTING

```
<160> NUMBER OF SEQ ID NOS: 25

<210> SEQ ID NO 1
<211> LENGTH: 12
<212> TYPE: PRT
<213> ORGANISM: HOMO SAPIENS

<400> SEQUENCE: 1

Ala Ala Val Leu Leu Pro Val Leu Leu Ala Ala Pro
1               5                   10

<210> SEQ ID NO 2
<211> LENGTH: 16
<212> TYPE: PRT
<213> ORGANISM: HOMO SAPIENS

<400> SEQUENCE: 2

Ala Ala Val Ala Leu Leu Pro Ala Val Leu Leu Ala Leu Leu Ala Pro
1               5                   10                  15

<210> SEQ ID NO 3
<211> LENGTH: 15
<212> TYPE: PRT
<213> ORGANISM: HOMO SAPIENS

<400> SEQUENCE: 3

Val Thr Val Leu Ala Leu Gly Ala Leu Ala Gly Val Gly Val Gly
1               5                   10                  15

<210> SEQ ID NO 4
<211> LENGTH: 199
<212> TYPE: PRT
<213> ORGANISM: HOMO SAPIENS

<400> SEQUENCE: 4

Met Glu Ala Arg Asp Lys Gln Val Leu Arg Ser Leu Arg Leu Glu Leu
1               5                   10                  15

Gly Ala Glu Val Leu Val Glu Gly Leu Val Leu Gln Tyr Leu Tyr Gln
                20                  25                  30

Glu Gly Ile Leu Thr Glu Asn His Ile Gln Glu Ile Asn Ala Gln Thr
            35                  40                  45

Thr Gly Leu Arg Lys Thr Met Leu Leu Leu Asp Ile Leu Pro Ser Arg
        50                  55                  60

Gly Pro Lys Ala Phe Asp Thr Phe Leu Asp Ser Leu Gln Glu Phe Pro
65                  70                  75                  80

Trp Val Arg Glu Lys Leu Lys Lys Ala Arg Glu Glu Ala Met Thr Asp
                85                  90                  95

Leu Pro Ala Gly Asp Arg Leu Thr Gly Ile Pro Ser His Ile Leu Asn
            100                 105                 110

Ser Ser Pro Ser Asp Arg Gln Ile Asn Gln Leu Ala Gln Arg Leu Gly
        115                 120                 125

Pro Glu Trp Glu Pro Met Val Leu Ser Leu Gly Leu Ser Gln Thr Asp
    130                 135                 140

Ile Tyr Arg Cys Lys Ala Asn His Pro His Asn Val Gln Ser Gln Val
145                 150                 155                 160
```

Val Glu Ala Phe Ile Arg Trp Arg Gln Arg Phe Gly Lys Gln Ala Thr
            165                 170                 175

Phe Gln Ser Leu His Asn Gly Leu Arg Ala Val Glu Val Asp Pro Ser
            180                 185                 190

Leu Leu Leu His Met Leu Glu
            195

<210> SEQ ID NO 5
<211> LENGTH: 94
<212> TYPE: PRT
<213> ORGANISM: HOMO SAPIENS

<400> SEQUENCE: 5

Met Glu Ala Arg Asp Lys Gln Val Leu Arg Ser Leu Arg Leu Glu Leu
1               5                   10                  15

Gly Ala Glu Val Leu Val Glu Gly Leu Val Leu Gln Tyr Leu Tyr Gln
            20                  25                  30

Glu Gly Ile Leu Thr Glu Asn His Ile Gln Glu Ile Asn Ala Gln Thr
        35                  40                  45

Thr Gly Leu Arg Lys Thr Met Leu Leu Leu Asp Ile Leu Pro Ser Arg
50                  55                  60

Gly Pro Lys Ala Phe Asp Thr Phe Leu Asp Ser Leu Gln Glu Phe Pro
65                  70                  75                  80

Trp Val Arg Glu Lys Leu Lys Lys Ala Arg Glu Glu Ala Met
                85                  90

<210> SEQ ID NO 6
<211> LENGTH: 79
<212> TYPE: PRT
<213> ORGANISM: HOMO SAPIENS

<400> SEQUENCE: 6

Asn Gln Leu Ala Gln Arg Leu Gly Pro Glu Trp Glu Pro Met Val Leu
1               5                   10                  15

Ser Leu Gly Leu Ser Gln Thr Asp Ile Tyr Arg Cys Lys Ala Asn His
            20                  25                  30

Pro His Asn Val Gln Ser Gln Val Val Glu Ala Phe Ile Arg Trp Arg
        35                  40                  45

Gln Arg Phe Gly Lys Gln Ala Thr Phe Gln Ser Leu His Asn Gly Leu
    50                  55                  60

Arg Ala Val Glu Val Asp Pro Ser Leu Leu Leu His Met Leu Glu
65                  70                  75

<210> SEQ ID NO 7
<211> LENGTH: 227
<212> TYPE: PRT
<213> ORGANISM: ARTIFICIAL SEQUENCE
<220> FEATURE:
<223> OTHER INFORMATION: SYNTHETIC CONSTRUCT

<400> SEQUENCE: 7

His His His His His His Gly Gly Gly Gly Ala Ala Val Leu Leu
1               5                   10                  15

Pro Val Leu Leu Ala Ala Pro Gly Gly Gly Gly Met Glu Ala Arg
            20                  25                  30

Asp Lys Gln Val Leu Arg Ser Leu Arg Leu Glu Leu Gly Ala Glu Val
        35                  40                  45

Leu Val Glu Gly Leu Val Leu Gln Tyr Leu Tyr Gln Glu Gly Ile Leu

```
            50                  55                  60
Thr Glu Asn His Ile Gln Glu Ile Asn Ala Gln Thr Thr Gly Leu Arg
 65                  70                  75                  80

Lys Thr Met Leu Leu Leu Asp Ile Leu Pro Ser Arg Gly Pro Lys Ala
                 85                  90                  95

Phe Asp Thr Phe Leu Asp Ser Leu Gln Glu Phe Pro Trp Val Arg Glu
            100                 105                 110

Lys Leu Lys Lys Ala Arg Glu Glu Ala Met Thr Asp Leu Pro Ala Gly
        115                 120                 125

Asp Arg Leu Thr Gly Ile Pro Ser His Ile Leu Asn Ser Ser Pro Ser
    130                 135                 140

Asp Arg Gln Ile Asn Gln Leu Ala Gln Arg Leu Gly Pro Glu Trp Glu
145                 150                 155                 160

Pro Met Val Leu Ser Leu Gly Leu Ser Gln Thr Asp Ile Tyr Arg Cys
                165                 170                 175

Lys Ala Asn His Pro His Asn Val Gln Ser Gln Val Val Glu Ala Phe
            180                 185                 190

Ile Arg Trp Arg Gln Arg Phe Gly Lys Gln Ala Thr Phe Gln Ser Leu
        195                 200                 205

His Asn Gly Leu Arg Ala Val Glu Val Asp Pro Ser Leu Leu Leu His
    210                 215                 220

Met Leu Glu
225

<210> SEQ ID NO 8
<211> LENGTH: 684
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 8
catcatcatc atcatcatgg gggggagga ggggcagctg tgcttctccc tgtgcttctt      60
gctgcacctg ggggggagg agggatggag gccagagaca acaagtact ccgctcactt     120 cgcctggagc tgggtgcaga ggtattggtg gagggactgg ttcttcagta cctctaccag    180
gaaggaatct tgacggaaaa ccatattcaa gaaatcaatg ctcaaaccac aggcctccgg    240
aaaacaatgc tcctgctgga tatcctacct tccaggggcc ctaaagcatt tgatacattc    300
ctagattccc tacaggagtt tccctgggtc agggagaagc tgaagaaggc aagggaagag    360
gccatgaccg acctgcctgc aggtgacaga ttgactggga tccctcgca catcctcaac    420 agctccccat cagaccggca gattaaccag ctggcccaga ggctgggccc tgagtgggag    480
cccatggtgc tgtctctggg actgtccag acggatatct accgctgtaa ggccaaccac    540
ccccacaacg tgcagtcgca ggtggtggag gccttcatcc gttggcggca gcgcttcggg    600
aagcaggcca ccttccagag cctgcacaac gggctgcggg ctgtggaggt ggaccctcg    660 ctgctcctgc acatgttgga gtga                                          684

<210> SEQ ID NO 9
<211> LENGTH: 600
<212> TYPE: DNA
<213> ORGANISM: HOMO SAPIENS

<400> SEQUENCE: 9
atggaggcca gagacaaaca agtactccgc tcacttcgcc tggagctggg tgcagaggta     60
```

-continued

```
ttggtggagg gactggttct tcagtacctc taccaggaag gaatcttgac ggaaaaccat    120
attcaagaaa tcaatgctca aaccacaggc ctccggaaaa caatgctcct gctggatatc    180
ctaccttcca ggggccctaa agcatttgat acattcctag attccctaca ggagtttccc    240
tgggtcaggg agaagctgaa gaaggcaagg gaagaggcca tgaccgacct gcctgcaggt    300
gacagattga ctgggatccc ctcgcacatc ctcaacagct ccccatcaga ccggcagatt    360
aaccagctgg cccagaggct gggccctgag tgggagccca tggtgctgtc tctgggactg    420
tcccagacgg atatctaccg ctgtaaggcc aaccacccc  acaacgtgca gtcgcaggtg    480
gtggaggcct tcatccgttg gcggcagcgc ttcgggaagc aggccacctt ccagagcctg    540
cacaacgggc tgcgggctgt ggaggtggac ccctcgctgc tcctgcacat gttggagtga    600
```

<210> SEQ ID NO 10
<211> LENGTH: 19
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 10
agtactccgc tcacttcgc                                                  19

<210> SEQ ID NO 11
<211> LENGTH: 19
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 11
ctgcaggcag gtcggtcat                                                  19

<210> SEQ ID NO 12
<211> LENGTH: 19
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 12
gaagaaatgg aagccagag                                                  19

<210> SEQ ID NO 13
<211> LENGTH: 18
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 13
ctgtaggcag ctcggctg                                                   18

<210> SEQ ID NO 14
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 14
cccgctccgc ctcctctcct t                                               21

<210> SEQ ID NO 15
<211> LENGTH: 19
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 15
ggcgcttctt ccgggtccg                                                19

<210> SEQ ID NO 16
<211> LENGTH: 19
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 16
gagagcatcc actgtcatg                                                19

<210> SEQ ID NO 17
<211> LENGTH: 20
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 17
ggagaaacat ctcacttgag                                               20

<210> SEQ ID NO 18
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 18
gcgacgtgga actggcagaa g                                             21

<210> SEQ ID NO 19
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 19
ggtacaaccc atcggctggc a                                             21

<210> SEQ ID NO 20
<211> LENGTH: 22
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 20
ttccatccag ttgccttctt gg                                            22

<210> SEQ ID NO 21
<211> LENGTH: 19
<212> TYPE: DNA
<213> ORGANISM: ARTIFICIAL SEQUENCE
<220> FEATURE:
<223> OTHER INFORMATION: SYNTHETIC CONSTRUCT

```
<400> SEQUENCE: 21
cttcatgtac tccaggtag                                               19

<210> SEQ ID NO 22
<211> LENGTH: 23
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 22
ctctagagca ccatgctaca gac                                          23

<210> SEQ ID NO 23
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 23
tggaatccag gggaaacact g                                            21

<210> SEQ ID NO 24
<211> LENGTH: 24
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 24
ttctttgcag ctccttcgtt gccg                                         24

<210> SEQ ID NO 25
<211> LENGTH: 24
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 25
tggatggcta cgtacatggc tggg                                         24
```

COMPOSITIONS AND METHODS FOR PREVENTING AND REDUCING INFLAMMATION AND TREATING DISORDERS ASSOCIATED WITH INFLAMMATION

CROSS-REFERENCE TO PRIORITY APPLICATION

This application claims the benefit of U.S. Provisional Application No. 62/121,685, filed Feb. 27, 2015, which is hereby incorporated by reference in its entirety, for all purposes, herein.

STATEMENT REGARDING FEDERALLY SPONSORED RESEARCH OR DEVELOPMENT

This invention was made with government support under Grant Nos. HL085833-05, HL069542-08, AA015752, and HL069765 awarded by the National Institutes of Health. The U.S. government has certain rights in the invention.

FIELD

The invention relates generally to the fields of biochemistry, vascular cell biology, immunology, molecular genetics, and medicine.

BACKGROUND

Inflammation represents a fundamental mechanism of diseases caused by microbial, autoimmune, metabolic, and physical insults. For example, the action of microbial insults on microvascular endothelial cells in severe microbial infections evolving into sepsis leads to endothelial dysfunction that contributes to major organ failure, disseminated intravascular coagulation, acute respiratory distress syndrome, acute kidney injury, and acute brain injury. There is a need for more effective therapeutics for preventing and treating inflammation-mediated diseases localized in cardiovascular, pulmonary, central nervous, gastrointestinal, hepatobiliary, and genitourinary systems. In particular, cardiovascular system diseases that are mediated by inflammation include atherosclerosis, aortic aneurysm formation, and hypertension.

BRIEF SUMMARY

The experimental results described herein provide new evidence that CRADD/RAIDD (caspase and receptor interacting protein adaptor with death domain/receptor interacting protein-associated ICH-1/CED-3 homologous protein with a death domain) plays a pivotal role in maintaining the integrity of endothelial monolayers. Increasing intracellular CRADD by delivery of a novel recombinant cell-penetrating CRADD protein (CP-CRADD) restored endothelial barrier function and suppressed the induction of Proinflammatory cytokine IL-6 and chemokine MCP-1 evoked by LPS and thrombin. Likewise, CP-CRADD enhanced barrier function in CRADD-sufficient endothelial cells. These results indicate that depletion of endogenous CRADD compromises endothelial barrier function in response to inflammatory signals. Mutations of the gene encoding CRADD protein are linked to Mental Retardation, autosomal recessive 34 (MRT 34). This disorder in its non-syndromic form affects individuals with significantly impaired cognitive function that precludes independent living and self care (Puffenberger E G, Jinks R N, Sougnez C et al. 2012 PLoS ONE 7 E28936). The compositions and methods described herein provide for the development of a novel treatment based on intracellular delivery of recombinant CRADD/RAIDD protein to compensate for the loss of endogenous physiologic form of CRADD. Replenishment of intracellular stores of CRADD is designed to counteract noxious signaling in inflammatory vascular and cognitive disorders, including central nervous system, respiratory, cardiovascular, gastrointestinal, and renal systems. The present invention relates to compositions, methods, and kits for preventing and reducing inflammation and preventing and treating diseases and disorders associated with inflammation. A composition including a recombinant protein having an MTM sequence and a CRADD sequence (CP-CRADD) may be administered to a subject for reduction and/or prevention of inflammation and treatment and prevention of associated diseases and disorders. Administration of a composition as described herein to a subject decreases inflammatory responses by blocking or reducing BLC10 (B-cell CLL/Lymphoma 10) activity and decreasing expression of interleukin (IL)-6 and monocyte chemoattractant protein-1 (MCP-1). BCL10 interacts with caspase recruitment domain (CARD) of the CARD membrane-associated guanylate kinase (CARMA) 1 in immune cells and CARMA 3 in non-immune cells including vascular endothelial cells as described below in 0026 "Inflammation and the adaptor CRADD/RAIDD".

Unless otherwise defined, all technical terms used herein have the same meaning as commonly understood by one of ordinary skill in the art to which this invention belongs.

As used herein, the terms "Membrane-translocating motif" and "MTM" mean a sequence derived from signal sequence hydrophobic region of human Fibroblast Growth Factor 4, other proteins or their fragments. Signal sequences that guide newly synthesized polypeptide chains from the ribosomal "tunnel" to the endoplasmic reticulum (ER) membrane have a tripartite structure that comprises an $NH_2$-terminal region (n region) and a hydrophobic h region of variable length followed by a cleavage site (c region) for signal peptidase located inside the lumen of ER. It is the signal sequence hydrophobic region (SSHR) that is endowed with membrane translocating activity (Veach R A et al receptor/Transporter-independent targeting of functional peptides across the plasma membrane. Journal of Biological Chemistry 2004, 279:11425-11431). SSHR-based membrane translocating motif (MTM) derived from human Fibroblast Growth Factor (FGF) 4, also known as Kaposi Growth factor, include the sequences AAVLLPVLLAAP (SEQ ID NO:1) and AAVALLPAVLLALLAP (SEQ ID NO:2). Another MTM derived from SSHR of integrin beta 3 includes the sequence VTVLALGALAGVGVG (SEQ ID NO:3) (Hawiger J. Non-invasive intracellular delivery of functional peptides and proteins Current Opinion in Chemical biology 1999, 3:69-94).

By the terms "recombinant cell-penetrating CRADD protein" and "CP-CRADD" is meant a protein including both a CRADD protein sequence and an MTM sequence that enables the protein to cross the plasma membrane of a subject's cells. A CP-CRADD protein is typically produced in a suitable expression system.

As used herein, "protein" and "polypeptide" are used synonymously to mean any peptide-linked chain of amino acids, regardless of length or post-translational modification, e.g., glycosylation or phosphorylation.

By the term "gene" is meant a nucleic acid molecule that codes for a particular protein, or in certain cases, a functional or structural RNA molecule.

As used herein, a "nucleic acid" or a "nucleic acid molecule" means a chain of two or more nucleotides such as RNA (ribonucleic acid) and DNA (deoxyribonucleic acid).

The terms "patient," "subject" and "individual" are used interchangeably herein, and mean a subject (e.g., vertebrate, mammalian (such as human), reptilian, piscine, avian, etc.) to be treated, diagnosed and/or to obtain a biological sample from.

As used herein, "bind," "binds," or "interacts with" means that one molecule recognizes and adheres to a particular second molecule in a sample or organism, but does not substantially recognize or adhere to other structurally unrelated molecules in the sample. Generally, a first molecule that "specifically binds" a second molecule has a binding affinity greater than about $10^8$ to $10^{12}$ moles/liter for that second molecule and involves precise "hand-in-a-glove" docking interactions that can be covalent and noncovalent (hydrogen bonding, hydrophobic, ionic, and van der Waals).

The term "labeled," with regard to a nucleic acid, protein, probe, cell or antibody, is intended to encompass direct labeling of the nucleic acid, protein, probe or antibody by coupling (i.e., physically or chemically linking) a detectable substance (detectable agent) to the nucleic acid, protein, probe, cell or antibody.

As used herein, the terms "therapeutic," and "therapeutic agent" are used interchangeably, and are meant to encompass any molecule, chemical entity, composition, drug, cell, therapeutic agent, chemotherapeutic agent, or biological agent capable of preventing and reducing inflammation and preventing and treating diseases and disorders associated with inflammation or any other condition. The term includes small molecule compounds, antisense reagents, siRNA reagents, antibodies, enzymes, peptides organic or inorganic molecules, cells, natural or synthetic compounds and the like.

As used herein, the term "treatment" is defined as the application or administration of a therapeutic agent to a patient or subject, or application or administration of the therapeutic agent to an isolated tissue or cell line from a patient or subject, who has a disease, a symptom of disease or a predisposition toward a disease, with the purpose to cure, heal, alleviate, relieve, alter, remedy, ameliorate, improve or affect the disease, the symptoms of disease, or the predisposition toward disease. Intracellular protein therapy is defined as application of cell-penetrating recombinant protein that is enabled to cross cell membrane of multiple cell types in blood and organs of a subject to replenish endogenous protein or provide functional form of such physiologic protein to individual carrying its defective (mutated) form. As such it is a facile alternative to gene replacement therapy.

Accordingly, described herein is a composition including a pharmaceutically acceptable carrier and a CP-CRADD in an amount sufficient to reduce or block BCL10 expression or activity and prevent or reduce inflammation and/or prevent or treat a condition associated with inflammation in a subject. Typically the amount is sufficient to reduce production of IL-6, monocyte chemoattractant protein 1 or other cytokines and chemokines produced by endothelial and epithelial cells. The CP-CRADD can include an MTM having the sequence AAVLLPVLLAAP (SEQ ID NO:1).

A device impregnated with a composition including a pharmaceutically acceptable carrier and a CP-CRADD in an amount sufficient to reduce or block BCL10 expression or activity and prevent or reduce inflammation and/or prevent or treat a condition associated with inflammation in a subject. The device can be a stent, scaffold, matrix, or inhaler.

A method of treating or preventing inflammation in a mammalian subject including administering a composition including a pharmaceutically acceptable carrier and a CP-CRADD in an amount sufficient to reduce or block BCL10 expression or activity and prevent or reduce inflammation and/or prevent or treat a condition associated with inflammation in a subject to the mammalian subject in an amount effective for preventing or reducing inflammation and/or preventing or treating a condition associated with inflammation in the mammalian subject. In the method, the subject can have or be predisposed to at least one of: hypertension, atherosclerosis, aortic aneurysm formation, neurovascular lesions, epithelial injury in respiratory, gastrointestinal, hepatobiliary, and genitourinary systems.

Administration of the composition extinguishes proinflammatory signaling in at least one of: endothelial cells, vascular smooth muscle cells, epithelial cells, lymphocytes and leukocytes in the subject. The subject can be a human. The CP-CRADD can include an MTM having the sequence AAVLLPVLLAAP (SEQ ID NO:1). The CP-CRADD can lack its death domain. The CP-CRADD can lack its CARD domain. The CP-CRADD can include an MTM having the sequence AAVALLPAVLLALLAP (SEQ ID NO:2). The CP-CRADD can include an MTM having the sequence VTVLALGALAGVGVG (SEQ ID NO:3).

Although compositions, kits, and methods similar or equivalent to those described herein can be used in the practice or testing of the present invention, suitable compositions, kits, and methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIGS. 1A and 1B show expression of CRADD and BCL10 in human and mouse endothelial cells and association of BCL10 with IRAK-1 in the proinflammatory TLR4 signaling pathway induced by LPS. CRADD mRNA and protein expression in endothelial cells was assessed by (FIG. 1A) RT-PCR and (FIG. 1B) immunoblot analysis. (FIG. 1C) BCL10 mRNA assessed by RT-PCR in endothelial cells. In RT-PCR analyses, human negative control (HNC) and mouse negative control (MNC) reactions were performed using human or mouse primers, respectively, without cDNA. In immunoblot analyses, mouse spleen and liver extracts derived from cradd+/+ and cradd−/− mice served as positive (+/+) and negative (−/−) controls for CRADD protein, respectively, and β-actin served as a cellular protein loading control. (FIG. 1D) Co-immunoprecipitation of BCL10 with IRAK-1 is stimulus- and time-dependent. Primary cradd+/+ Lung Microvascular Endothelial Cells (LMEC) or human ST1.6 R endothelial cells were stimulated with 1 µg/ml LPS for the indicated times. Protein complexes precipitated with anti-IRAK-1 (IP) from cell lysates were immunoblotted (TB) with antibodies to the indicated proteins. All gels and blots shown are representative of three independent experiments.

FIGS. 2A, 2B, 2C, 2D, and 2E show expression of IL-6 induced by proinflammatory agonists in CRADD-depleted endothelial cells is dependent on BCL10. (FIG. 2A) CRADD and (FIG. 2B) BCL10 protein knockdown (K/D)

induced by shRNA transduction in LEII cells was assessed by immunoblot analysis after 96 h. Shown are immunoblots and means+SD of proteins from at least 3 independent immunoblots normalized to β-actin and GAPDH cellular protein loading controls for CRADD and BCL10, respectively, with calculation of percent suppression of CRADD and BCL10. (FIG. 2C and FIG. 2D) LEII cells (mouse lung capillary) were transduced with control, CRADD and/or BCL10 shRNA as indicated for 96 h then treated with 100 ng/ml LPS (FIG. 2C) or 1.5 U/ml thrombin (FIG. 2D). IL-6 in culture media was measured 24 h after stimulation. Results are presented as means+SD from three independent experiments performed in duplicate (***$p<0.0001$ by t test) (FIG. 2E) LEII cells were transduced with control, or CRADD shRNA as indicated for 96 h then treated with 10 ng/ml LPS for 1 h. Nuclear translocation of NFκB p65/RelA (p65) was assessed by immunofluorescence staining and by immunoblot analysis of nuclear extracts. Shown are immunofluorescence and immunoblot images representative of at least 3 independent experiments. Quantification of immunoblots are based on analysis of 6 lanes and shown as means+SD of proteins normalized to TBP nuclear protein loading control in that lane. Magnification 40×, scale bars=5 μm. (*$p<0.05$ by t test).

(FIG. 3A) In unstimulated cells, CRADD expression is reduced by shRNA targeting CRADD but not by non-target scrambled shRNA. (FIG. 3B) LPS and (FIG. 3C) thrombin stimulation increased transcripts for TNFα, IL-6, and IL-1a in cells not tranduced with shRNA. Knockdown of CRADD with shRNA targeting CRADD further increases mRNA expression. Treatment with CP-CRADD reduces expression to that of cells without CRADD knockdown. Gels shown are representative of 3 independent experiments. Graphs represent quantification of bands from three gels. Values from unstimulated samples were set as background and NL or NT bands were set to 1. Fold change from stimulated non-transduced samples (NL or NT) are shown as +SD from three independent experiments (NS=not significant, *$p<0.05$, $p<0.01$, *$p<0.001$ by t test).

(FIG. 4A) Schematic representation of full-length wild-type CRADD, showing different functional domains of the protein including the CARD domain (green) and Death domain (blue). Non-CP-CRADD lacks the MTM but contains an N-terminal 6×His tag (black) needed for affinity purification of recombinant protein while CP-CRADD contains the N-terminal 6×His tag (black), followed by a 12 amino acid MTM (red). (FIG. 4B) Protein staining with Coomassie blue displays recombinant non-CP-CRADD (25 kDa) and CP-CRADD (26 kDa) proteins. BSA is shown between them for size reference. (FIG. 4C) Tracking intracellular delivery of CP-CRADD by protease resistance and quantitative immunoblotting. Left, lysates from ST1.6R cells that were incubated for 1 h with equimolar doses (10 μM) of non-CP-CRADD or CP-CRADD, then treated with proteinase K to remove extracellular proteins. Right, recombinant protein preparations added to cells. All samples were run on the same gel and immunoblotted with an anti-CRADD antibody that recognizes both endogenous and recombinant CRADD in cell lysates as indicated. Immunoblot is representative of two independent experiments performed in triplicate.

(FIG. 5A) After 2 h treatment of control or CRADD K/D LEII cells with equimolar doses (6 μM) of non-CP-CRADD or CP-CRADD, cells were stimulated with 100 ng/ml LPS (left) or 1.5 U/ml thrombin (right). (FIG. 5B) LMEC were isolated from cradd+/+ and cradd−/− mice. Cells were stimulated with 100 ng/ml LPS. (FIG. 5C) LMEC isolated from cradd+/+ and cradd−/− mice were treated for 3 h with equimolar doses (11 μM) of non-CP-CRADD or CP-CRADD, then stimulated with 100 ng/ml LPS. (FIG. 5D) Human ST1.6R endothelial cells were treated for 3 h with equimolar doses (11 μM) of non-CP-CRADD or CP-CRADD, then stimulated as in A. IL-6 and MCP-1 in culture media were measured 24 h after stimulation. Results are presented as means+SD from three independent experiments performed in duplicate (*$p<0.05$, $p<0.01$, *$p<0.0001$ by t test).

(FIG. 6A-C) LMEC isolated from cradd+/+ and cradd−/− mice were grown to confluence on Transwell inserts and left unstimulated (FIG. 6A) or stimulated with 1 μg/ml LPS for 24 h (FIG. 6B) or 10 U/ml thrombin for 6 h (FIG. 6C). (FIG. 6D-FIG. 6F) permeability of 10 kDa compared to 70 kDa FITC-Dextran. LMEC isolated from cradd−/− mice (FIG. 6D and FIG. 6E) were stimulated with LPS (FIG. 6D) or thrombin (FIG. 6E) as in FIG. 6B and FIG. 6C. (F) human ST1.6R cells were stimulated with 30 U/ml thrombin for 20 min. (G and H) LMEC isolated from cradd−/− mice were treated for 3 h with equimolar doses (12 μM) of non-CP-CRADD or CP-CRADD, then stimulated with LPS (FIG. 6G) or thrombin (FIG. 6H) as in FIG. 6B and FIG. 6C. (I) Human ST1.6R cells were stimulated with thrombin as in FIG. 6F. To assess permeability, FITC-Dextran (10 kDa in FIG. 6A-FIG. 6C and FIG. 6G-FIG. 6I) was added to each insert and fluorescence in the lower chamber measured at the indicated times. Results are presented as means±SD in relative fluorescence units (RFU) from three independent experiments performed in duplicate (p values shown were determined by t test of the AUCs from 3 independent experiments).

FIGS. 7A, 7B, 7C, 7D, 7E, and 7F show F-actin polymerization and cellular contraction are enhanced in cradd−/− as compared to cradd+/+ LMEC monolayers after stimulation with LPS or thrombin. LMEC isolated from cradd+/+ and cradd−/− mice were grown to confluence then left unstimulated (FIG. 7A and FIG. 7B), or stimulated with 1 μg/ml LPS for 24 h (FIG. 7C and FIG. 7D) or 10 U/ml thrombin for 6 h (FIG. 7E and FIG. 7F). Cells were stained with Alexa 488-labeled phalloidin (green) to visualize F-actin. Nuclei are counterstained with DAPI (blue). Arrows indicate gaps in the monolayer caused by cellular retraction in stimulated cells. Images are representative of at least 3 independent experiments. Magnification 63×, scale bars=1 μm.

FIGS. 8A, 8B, 8C, 8D, 8E, and 8F show CRADD deficiency exacerbates the loss of monolayer integrity in LPS- or thrombin-stimulated LMEC monolayers analyzed by immunofluorescence of VE-cadherin and p120. LMEC isolated from cradd+/+ and cradd−/− mice were grown to confluence then left unstimulated (FIG. 8A and FIG. 8B), or stimulated with 1 μg/ml LPS for 24 h (FIG. 8C and FIG. 8D) or 10 U/ml thrombin for 6 h (FIG. 8E and FIG. 8F). Cells were immunostained with p120 (red) and VE-cadherin (green). Nuclei are counterstained with DAPI (blue). Arrows indicate disruption of both proteins in cell membranes of stimulated cradd−/− LMEC. Images are representative of at least 3 independent experiments. Magnification 63×, scale bars=1 μm.

DETAILED DESCRIPTION

Figure 3A:
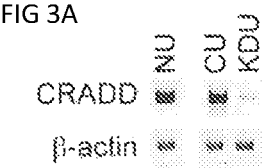
FIGS. 3A, 3B, and 3C show that endothelial CRADD suppresses mRNA expression of cytokines TNFα, IL-6, and IL-1a in response to proinflammatory agonists. Murine lung capillary endothelial LEII cells were left non-transduced (N), or were transduced with shRNA for CRADD knockdown (KD), or with scrambled control shRNA (FIG. 3C). After 96 h, control and CRADD K/D LEII cells were left unstimulated (U) or stimulated with 1 μg/ml LPS (L) or with 10 U/ml thrombin (T) for 24 h. Some CRADD K/D cells were treated with CP-CRADD (CP) or non-CP-CRADD (non-CP) for 2 h before stimulation. β-actin was used as a control for RT-PCR.

Described herein are compositions, kits and methods for preventing and reducing inflammation and preventing and treating diseases and disorders associated with inflammation. The compositions, kits and methods include a recombinant cell-penetrating CRADD protein (CP-CRADD) and are a novel treatment for inflammatory vascular disorders and other disorders associated with functionally abnormal form of CRADD protein or its deficiency. In the experiments described herein, the CP-CRADD protein included an MTM having the sequence AAVLLPVLLAAP (SEQ ID NO:1). However, any suitable MTM can be used (e.g., an MTM having the sequence AAVALLPAVLLALLAP (SEQ ID NO:2).

Inflammation and the Adaptor CRADD/RAIDD

To counteract the deleterious action of proinflammatory cytokines and chemokines, an intracellular negative feedback system has evolved to "put on the brakes" and limit the duration and strength of proinflammatory signaling. This system is comprised of intracellular physiologic proteins that control excessive inflammatory responses. They include interleukin 1-receptor-associated kinase (IRAK)-M, an inhibitory member of the IRAK family, the inhibitor of nuclear factor kappa B (NFκB) transcription factors IκB, the suppressors of cytokine signaling (SOCS) proteins that inhibit activated STAT transcription factors, and the ubiquitin-modifying enzyme A20. Recently, the "death" adaptor caspase and receptor interacting protein adaptor with death domain/receptor interacting protein-associated ICH-1/CED-3 homologous protein with a death domain (CRADD/RAIDD), hereafter designated as CRADD, was added to this list. CRADD negatively regulates NFκB-dependent cytokine and chemokine expression in T cells by targeting the NH$_2$-terminal caspase recruitment domain (CARD) of B-cell CLL/Lymphoma 10 (BCL10). In immune cells, the CARD of BCL10 functions as an oligomerization region and interacts with the CARD of CARD membrane-associated guanylate kinase (CARMA) 1 (Lin, Q., Liu, Y., Moore, D. J., Elizer, S. K., Veach, R. A., Hawiger, J., and Ruley, H. E. (2012) Cutting Edge: The "Death" Adaptor CRADD/RAIDD Targets BCL10 and Suppresses Agonist-Induced Cytokine Expression in T Lymphocytes. *The Journal of Immunology* 188, 2493-2497; Paul, S., and Schaefer, B. C. (2013) A new look at T cell receptor signaling to nuclear factor-kappaB. *Trends in immunology* 34, 269-281), which is required for activation of the NFκB pathway. In non-immune cells, such as endothelial and epithelial cells, a CARMA3 signalosome containing BCL10 and mucosa-associated lymphoid tissue lymphoma translocation protein 1 (MALT1), operates to regulate the NFκB signaling pathway. Disruption of the CARMA3 signalosome by genetic deletion of Bcl10 leads to dramatic reduction of vascular inflammation, illustrating that BCL10 is an essential component of the signaling complex.

The CARMA3 signalosome also modulates endothelial barrier function in response to proinflammatory agonists that induce increased vascular permeability. Induction of vascular permeability causes swelling, one of the four classic signs of inflammation, due to the action of proinflammatory agonists sensed by their cognate receptors expressed on microvascular endothelial cells. The CARMA3 signalosome amplifies signaling in response to proinflammatory agonists and mediates stimulus-dependent nuclear reprogramming, which depends on transcription factors NFκB and AP-1. Thus, the CARMA3 signalosome plays a pivotal role in shifting microvascular endothelial cells from a resting to activated state, integrating signaling pathways evoked by recognition of diverse agonists. This signaling promulgates an inflammatory response, based in part on disruption of endothelial barrier function by altering cell-cell junctions that include adherens junctions and tight junctions. These mainstays of endothelial monolayer integrity dynamically guard barrier function in the major organs that contain an extensive network of microcirculation, such as lungs, kidneys, liver, and brain. Vascular endothelial cadherin (VE-cadherin) is a strictly endothelial specific cell adhesion molecule and the major determinant of endothelial cell contact integrity. Its adhesive function requires association with the cytoplasmic catenin protein p120. LPS and thrombin induce F-actin reorganization and subsequent reductions in VE-cadherin at endothelial cell junctions, resulting in increased vascular permeability. CRADD's target, BCL10, and its effector, NFκB, have been implicated in mediating these changes.

As described in the Example below, the potential role of CRADD in endothelial cell homeostasis was analyzed by employing three approaches: (i) reduction of CRADD expression in murine endothelial cells with shRNA, (ii) analysis of microvascular endothelial cells isolated from CRADD-deficient mice, and (iii) intracellular delivery of a novel recombinant cell-penetrating CRADD protein homolog (CP-CRADD) to CRADD-deficient and sufficient endothelial cells. A protective role was documented for CRADD in maintaining the permeability barrier of primary lung microvascular endothelial cells (LMEC) by demonstrating increased agonist-induced permeability of cradd−/− LMEC monolayers compared to cradd+/+ LMEC monolayers. Moreover, treatment with CP-CRADD restored barrier function in endothelial monolayers of human and murine cells challenged with proinflammatory agonists.

Biological and Chemical Methods

Methods involving conventional molecular biology techniques are described herein. Such techniques are generally known in the art and are described in detail in methodology treatises such as Sambrook et al. ed., (2001) Molecular Cloning: A Laboratory Manual, 3rd ed., vol. 1-3, Cold Spring Harbor Laboratory Press, Cold Spring Harbor, N.Y.; and Ausubel et al. ed., (1992) (with periodic updates) Current Protocols in Molecular Biology, ed., Greene Publishing and Wiley-Interscience, New York.

An amino acid sequence for full-length human CRADD is:

(SEQ ID NO: 4)
MEARDKQVLRSLRLELGAEVLVEGLVLQYLYQEGILTENHIQEINAQTTG

LRKTMLLLDILPSRGPKAFDTFLDSLQEFPWVREKLKKAREEAMTDLPAG

-continued
DRLTGIPSHILNSSPSDRQINQLAQRLGPEWEPMVLSLGLSQTDIYRCKA

NHPHNVQSQVVEAFIRWRQRFGKQATFQSLHNGLRAVEVDPSLLLHMLE.

An amino acid sequence for the CARD domain (amino acids 1-94) is:

(SEQ ID NO: 5)
MEARDKQVLRSLRLELGAEVLVEGLVLQYLYQEGILTENHIQEINAQTTG

LRKTMLLLDILPSRGPKAFDTFLDSLQEFPWVREKLKKAREEAM

An amino acid sequence for a Death Domain (amino acids 121-200) is:

(SEQ ID NO: 6)
NQLAQRLGPEWEPMVLSLGLSQTDIYRCKANHPHNVQSQVVEAFIRWRQR

FGKQATFQSLHNGLRAVEVDPSLLLHMLE

An amino acid sequence for a full-length Human CP-CRADD is:

(SEQ ID NO: 7)
HHHHHHGGGGGAAVLLPVLLAAPGGGGGMEARDKQVLRSLRLELGAEVLV

EGLVLQYLYQEGILTENHIQEINAQTTGLRKTMLLLDILPSRGPKAFDTF

LDSLQEFPWVREKLKKAREEAMTDLPAGDRLTGIPSHILNSSPSDRQINQ

LAQRLGPEWEPMVLSLGLSQTDIYRCKANHPHNVQSQVVEAFIRWRQRFG

KQATFQSLHNGLRAVEVDPSLLLHMLE

A nucleic acid sequence encoding a full-length Human CP-CRADD is:

(SEQ ID NO: 8)
Catcatcatcatcatcatggggggggaggaggggcagctgtgcttctccc tgtgcttcttgctgcacctggggggggaggagggatggaggccagagaca aacaagtactccgctcacttcgcctggagctgggtgcagaggtattggtg gagggactggttcttcagtacctctaccaggaaggaatcttgacggaaaa ccatattcaagaaatcaatgctcaaaccacaggcctccggaaaacaatgc tcctgctggatatcctaccttccaggggccctaaagcatttgatacattc ctagattccctacaggagtttccctgggtcagggagaagctgaagaaggc aagggaagaggccatgaccgacctgcctgcaggtgacagattgactggga tcccctcgcacatcctcaacagctccccatcagaccggcagattaaccag ctggcccagaggctgggccctgagtgggagcccatggtgctgtctctggg actgtcccagacggatatctaccgctgtaaggccaaccaccccacaacg tgcagtcgcaggtggtggaggccttcatccgttggcggcagcgcttcggg aagcaggccaccttccagagcctgcacaacgggctgcgggctgtggaggt ggaccctcgctgctcctgcacatgttggagtga.

A nucleic acid sequence encoding a full-length human CRADD is:

(SEQ ID NO: 9)
Atggaggccagagacaaacaagtactccgctcacttcgcctggagctgg gtgcagaggtattggtggagggactggttcttcagtacctctaccagga aggaatcttgacggaaaaccatattcaagaaatcaatgctcaaaccaca ggcctccggaaaacaatgctcctgctggatatcctaccttccaggggcc ctaaagcatttgatacattcctagattccctacaggagtttccctgggt cagggagaagctgaagaaggcaagggaagaggccatgaccgacctgcct gcaggtgacagattgactgggatcccctcgcacatcctcaacagctccc catcagaccggcagattaaccagctggcccagaggctgggccctgagtg ggagcccatggtgctgtctctgggactgtcccagacggatatctaccgc tgtaaggccaaccaccccacaacgtgcagtcgcaggtggtggaggcct tcatccgttggcggcagcgcttcgggaagcaggccaccttccagagcct gcacaacgggctgcgggctgtggaggtggaccctcgctgctcctgcac atgttggagtga.

Compositions for Preventing and Reducing Inflammation and Preventing and Treating Diseases and Disorders Associated with Inflammation in a Subject Compositions (e.g., pharmaceutical compositions) described herein for preventing and treating inflammation and diseases and disorders associated with inflammation include a therapeutically effective amount of a composition including a pharmaceutically acceptable carrier and a recombinant protein having a full-length CRADD sequence and an MTM sequence or truncated CRADD sequence and an MTM sequence. The recombinant protein (e.g., CP-CRADD) is in an amount sufficient for reducing or blocking BCL10 expression or activity and preventing or reducing inflammation and/or preventing or treating a condition associated with inflammation in a subject. The amount is also typically sufficient to reduce IL-6 expression. In one example of a CP-CRADD protein, the CP-CRADD includes an MTM having the sequence AAVLLPVLLAAP (SEQ ID NO:1). However, any peptide sequence that is enabling translocation of recombinant CRADD protein or its fragments into cell interior can be used as an MTM in the compositions and methods described herein. Examples of additional MTMs include AAVALLPAVLLALLAP (SEQ ID NO:2) and VTVLALGALAGVGVG (SEQ ID NO:3). Any mimetics, derivatives, or homologs of such MTMs may be used in the compositions, methods, and kits disclosed herein. Generation and use of the MTM having the sequence AAVLLPVLLAAP (SEQ ID NO:1) is described in Hawiger J. Curr. Opin. Chem. Biol 1999, 3:69-94, and U.S. Pat. Nos. 8,420,096 and 8,324,148. These patents are incorporated by reference herein in their entireties.

The CRADD sequence is typically a human CRADD sequence, and the human CRADD sequence is known. Any derivatives, analogue or homologs of the human CRADD sequence can be used.

In some embodiments, an additional therapeutic agent such as CP-SOCS3 or other anti-inflammatory and cytoprotective agent may be administered at the same time, sequentially, or during the treatment course of the CP-CRADD protein. In such embodiments, any suitable existing or yet to be developed anti-inflammatory and cytoprotective compound agent may be administered with a composition including a CP-CRADD protein.

In some embodiments, devices are coated or impregnated with a composition as described herein before implantation in a subject in need thereof. Such devices include a stent, scaffold, matrix, polymers, subcutaneous osmotic pumps, sponges, and inhalers for intanasal delivery. Applications for use of such coated or impregnated devices include slow-release polymer impregnated with CP-CRADD protein used for coating endovascular stents and catheters.

Methods of Preventing and Reducing Inflammation and Preventing and Treating Diseases and Disorders Associated with Inflammation in a Subject A typical method of preventing and reducing inflammation and preventing and treating diseases and disorders associated with inflammation in a subject (e.g., mammalian subject) includes administering a composition including a pharmaceutically acceptable carrier and a recombinant protein having a CRADD sequence and an MTM sequence to the mammalian subject in an amount effective or sufficient for reducing or blocking BCL10 activity or expression and preventing or reducing inflammation and/or preventing or treating a condition associated with inflammation in a subject. The amount is also typically sufficient to reduce IL-6 expression in the mammalian subject. In one example of the method, the subject has or is predisposed to at least one of: hypertension, atherosclerosis, and aortic aneurysm formation. Generally, administration of the composition extinguishes proinflammatory signaling in endothelial cells and/or vascular smooth muscle cells in the subject (e.g., human). In a typical method, the CP-CRADD includes an MTM having the sequence AAVLLPVLLAAP (SEQ ID NO:1), however, any suitable MTM can be used.

In one embodiment, the invention provides a method of monitoring treatment progress. The method includes the step of determining a level of diagnostic marker such as C-reactive Protein (CRP), IL-6, IL-8, IL-12, IL-18, etc. (e.g., any target delineated herein modulated by a composition or agent described herein, a protein or indicator thereof, etc.) or diagnostic measurement (e.g., screen, assay) in a subject suffering from or susceptible to a disorder or symptoms thereof associated with inflammation in which the subject has been administered a therapeutic amount of a composition as described herein for treating the disease or symptoms thereof. The level of marker determined in the method can be compared to known levels of marker in either healthy normal controls or in other afflicted patients to establish the subject's disease status. In preferred embodiments, a second level of marker (e.g., CRP, IL-6, IL-8, IL-12, IL-18, etc.) in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

Also described herein are diagnostic and theranostic methods useful to determine whether the subject is susceptible to the treatment methods of the invention. The term "theranostics" generally refers to therapy-specific diagnostics, which is the use of diagnostic testing to diagnose the disease, choose the correct treatment regime for that disease, and monitor the patient response to therapy. Theranostic tests can be used to predict and assess a response to the therapeutic agent (e.g., drug) in individual patients, and are designed to improve therapeutic agent efficacy by selecting patients for treatments that are particularly likely to benefit from the treatments. Theranostic tests are also designed to improve therapeutic agent safety by identifying patients that may suffer adverse side effects from the treatment.

Kits

Described herein are kits for preventing and reducing inflammation and preventing and treating diseases and disorders associated with inflammation in a subject. A typical kit includes: a composition including a pharmaceutically acceptable carrier and a recombinant protein having a CRADD sequence and an MTM sequence in an amount effective or sufficient for reducing or blocking BCL10 expression or activity and preventing or reducing inflammation and/or preventing or treating a condition associated with inflammation in a subject (and typically also sufficient to reduce IL-6 expression), as well as packaging, and instructions for use. In some embodiments, an additional therapeutic agent such as an CP-SOCS3 or other anti-inflammatory and cytoprotective agent may be included in the kit. Optionally, kits may also contain one or more of the following: containers which include positive controls, containers which include negative controls, photographs or images of representative examples of positive results and photographs or images of representative examples of negative results.

Administration of Pharmaceutical Compositions

The administration of a composition including a CP-CRADD in an amount effective for preventing and reducing inflammation and preventing and treating diseases and disorders associated with inflammation may be by any suitable means that results in a concentration of the therapeutic that is effective in reducing or blocking BCL10 expression or activity and typically, also effective in reducing IL-6 expression. In some embodiments, an additional compound such as a CP-SOCS3 or other anti-inflammatory and cytoprotective agent may be administered. The CP-CRADD may be contained in any appropriate amount in any suitable carrier substance, and is generally present in an amount of 1-95% by weight of the total weight of the composition. The composition may be provided in a dosage form that is suitable for local or systemic administration (e.g., parenteral, subcutaneously, intravenously, intramuscularly, intranasally, or intraperitoneally). The pharmaceutical compositions may be formulated according to conventional pharmaceutical practice (see, e.g., (Gennaro, A. R. ed. (2000) Remington: The Science and Practice of Pharmacy (20th ed.), Lippincott Williams & Wilkins, Baltimore, Md.; Swarbrick, J. and Boylan, J. C. eds. (1988-1999) Encyclopedia of Pharmaceutical Technology, Marcel Dekker, New York).

Compositions as described herein may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. In one embodiment, a stent or scaffold that is impregnated with a composition as described herein is implanted in the subject. The composition may be administered orally in sublingual form or with a coating protecting the composition from gastrointestinal peptidases. The formulation and preparation of such compositions are well known to those skilled in the art of pharmaceutical formulation. Formulations can be found in Gennaro supra.

Compositions for parenteral use may be provided in unit dosage forms (e.g., in single-dose ampoules), or in vials containing several doses and in which a suitable preservative may be added. The composition may be in the form of a solution, a suspension, an emulsion, an infusion device, or a delivery device (e.g., a stent, scaffold, matrix, etc.) for implantation, or it may be presented as a dry powder to be reconstituted with water or another suitable vehicle before use. Apart from the active agent that prevents or reduces inflammation and/or prevents or treats diseases and disorders associated with inflammation for example, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

As indicated above, the pharmaceutical compositions described herein may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Materials for use in the preparation of microspheres and/or microcapsules are, e.g., biodegradable/bioerodible polymers such as polygalactin, poly-(isobutyl cyanoacrylate), poly(2-hydroxyethyl-L-glutamine), and poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Formulations for oral use include sublingual tablets containing the active ingredient(s) (e.g., a CP-CRADD) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

The solid tablet compositions may include a coating adapted to protect the composition from unwanted chemical changes, (e.g., chemical degradation prior to the release of the active therapeutic substance). The coating may be applied on the solid dosage form in a similar manner as that described in Swarbrick J. and Boylan, J. C. supra. At least two therapeutics for preventing and reducing inflammation and preventing and treating diseases and disorders associated with inflammation (e.g., a CP-CRADD and a CP-SOCS3 or other anti-inflammatory and cytoprotective agent) may be mixed together in the tablet, or may be partitioned. In one example, the first active therapeutic is contained on the inside of the tablet, and the second active therapeutic is on the outside, such that a substantial portion of the second active therapeutic is released prior to the release of the first active therapeutic.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment. Compositions as described herein can also be formulated for inhalation and topical applications. Combinations of two or more therapeutics are expected to be advantageously synergistic. Therapeutic combinations that decrease inflammatory responses by blocking or reducing BLC10 activity and decreasing expression of IL-6, for example, are identified as useful in the compositions, methods, and kits described herein.

The therapeutic methods described herein in general include administration of a therapeutically effective amount of a composition described herein to a subject (e.g., animal) in need thereof, including a mammal, particularly a human. Such treatment will be suitably administered to subjects, particularly humans, suffering from, having, susceptible to, or at risk for inflammation and diseases and disorders associated with inflammation. Determination of those subjects "at risk" can be made by any objective or subjective determination by a diagnostic test or opinion of a subject or physician.

Effective Doses

The compositions (pharmaceutical compositions) described herein are preferably administered to an animal (e.g., mammalian (such as human, ovine, bovine, canine, porcine, equine, etc.), reptilian, piscine, avian, etc.) in an effective amount, that is, an amount capable of producing a desirable result in a treated animal (e.g., reducing or preventing inflammation). Such a therapeutically effective amount can be determined according to standard methods. Toxicity and therapeutic efficacy of the compositions utilized in methods of the invention can be determined by standard pharmaceutical procedures. As is well known in the medical and veterinary arts, dosage for any one subject depends on many factors, including the subject's size, body surface area, age, the particular composition to be administered, time and route of administration, general health, and other drugs being administered concurrently.

EXAMPLES

The present invention is further illustrated by the following specific examples. The examples are provided for illustration only and should not be construed as limiting the scope of the invention in any way.

Example 1—The Adaptor CRADD/RAIDD Controls Activation of Endothelial Cells by Proinflammatory Stimuli A hallmark of inflammation, increased vascular permeability, is induced in endothelial cells by multiple agonists through stimulus-coupled assembly of the CARMA3 signalosome, which contains the adaptor protein BCL10. Previously, it was reported that BCL10 in immune cells is targeted by the "death" adaptor CRADD/RAIDD (CRADD), which negatively regulates nuclear factor kappa B (NFκB)-dependent cytokine and chemokine expression in T cells (Lin Q, Liu Y, Moore D J et al (2012) J. Immunol. 188:2493-2497). This novel anti-inflammatory CRADD-BCL10 axis prompted the analysis described below of CRADD expression and its potential anti-inflammatory action in non-immune cells. This study was focused on microvascular endothelial cells since they play a key role in inflammation. It was found that CRADD-deficient murine endothelial cells display heightened BCL10-mediated expression of the pleotropic proinflammatory cytokine IL-6 and chemokine monocyte chemoattractant protein-1 (MCP-1/CCL2) in response to LPS and thrombin. Moreover, these agonists also induce significantly increased permeability in cradd−/−, as compared to cradd+/+, primary murine endothelial cells. CRADD-deficient cells displayed more F-actin polymerization with concomitant disruption of adherens junctions. In turn, increasing intracellular CRADD by delivery of a novel recombinant cell-penetrating CRADD protein (CP-CRADD) restored endothelial barrier function and suppressed the induction of IL-6 and MCP-1 evoked by LPS and thrombin. Likewise, CP-CRADD enhanced barrier function in CRADD-sufficient endothelial cells. These results indicate that depletion of endogenous CRADD compromises endothelial barrier function in response to inflammatory signals. Thus, a novel function was discovered for CRADD in endothelial cells as an inducible suppressor of BCL10, a key mediator of responses to proinflammatory agonists. As CRADD is also expressed in epithelial cells, which express its target BCL10, this novel axis can be modulated by CP-CRADD administered to epithelial cells lining airways, gastrointestinal system, and skin.

Experimental Procedures

Mice-Wild-type cradd+/+ and knockout cradd−/− mice were generated and maintained as previously described (Lin, Q., Liu, Y., Moore, D. J., Elizer, S. K., Veach, R. A., Hawiger, J., and Ruley, H. E. (2012) Cutting Edge: The "Death" Adaptor CRADD/RAIDD Targets BCL10 and Suppresses Agonist-Induced Cytokine Expression in T Lymphocytes. *The Journal of Immunology* 188, 2493-2497). All work with animals was carried out in strict accordance with the recommendations in the Guide for the Care and Use of Laboratory Animals of the National Institutes of Health, and approved by the Vanderbilt University Institutional Animal Care and Use Committee.

Endothelial Cell Culture-Primary human umbilical vein endothelial cells (HUVEC) were purchased from ScienCell and cultured in ECM (ScienCell). Primary murine LMEC were isolated from cradd+/+ and cradd−/− mice using a lung dissociation kit and purified by immunomagnetic separation, with anti-CD45-conjugated and anti-CD31-conjugated MicroBeads according to protocols provided by the manufacturer (Miltenyi Biotec), then cultured in collagen-coated tissue culture dishes with EBM-2 (Lonza) supplemented with 5% heat-inactivated FBS, 25 µg/ml endothelial mitogen (EM, Biomedical Technologies) and 1% penicillin/streptomycin solution (pen/strep, Mediatech). The human lung microvascular endothelial cell line HPMEC-ST1.6R was cultured in M199 (Mediatech) supplemented with 10% heat-inactivated FBS, 25 µg/ml EM, 50 µg/ml heparin (Sigma), and 1% pen/strep. EA.hy926, EOMA, and SVEC4-10 cell lines were purchased from ATCC. LEII and cell lines from ATCC were cultured in DMEM (Mediatech) supplemented with 10% heat-inactivated FBS and 1% pen/strep.

Immunoprecipitation and Immunoblot analysis-Antibodies to CRADD (Proteintech Group), BCL10 and NFκB p65/RelA (Santa Cruz) were used for immunoblot analyses. GAPDH, β-actin or TATA binding protein (TBP) antibodies (Abcam) were used for normalization of cytosolic and nuclear extracts as indicated in figure legends. Complexes were immunoprecipitated from cell lysates with antibody to IRAK-1 (Santa Cruz) and protein A/G agarose beads (Thermo) then analyzed by quantitative immunoblotting using antibodies to IRAK-1 and BCL10. All immunoblots were analyzed with LI-COR's Odyssey Infrared Imaging System as previously described.

Lentiviral shRNA knockdown of CRADD and BCL10 in endothelial cells-Lentiviral packaging and shRNA transduction were performed as previously described (Qiao, H., and May, J. M. (2012) Interaction of the transcription start site core region and transcription factor YY1 determine ascorbate transporter SVCT2 exon 1a promoter activity. PloS one 7, e35746). CRADD and BCL10 knockdown (K/D) efficiency was assessed at the transcript and protein level after 96 h, when shRNA-mediated knockdown experiments were performed.

RT-PCR analysis-Total RNA was isolated for RT-PCR analysis using TRIZOL reagent (GIBCO) and reverse-transcribed using the iScript cDNA synthesis kit (Bio-Rad). Targets were amplified by PCR using PCR Master Mix (Promega) with specific primers listed in Table I for indicated protein mRNAs. PCR products were separated on 1% agarose gels. Ethidium bromide-stained gels were imaged on a Gel Doc EZ Imager (Bio-Rad) and analyzed with Image Lab 5.0 software to quantify bands.

TABLE I

Oligonucleotide PCR primer sequences used in the current study

| Gene | | Primer sequences (5' to 3') |
|---|---|---|
| hCRADD | Forward | 5-AGTACTCCGCTCACTTCGC-3 (SEQ ID NO: 10) |
| | Reverse | 5-CTGCAGGCAGGTCGGTCAT-3 (SEQ ID NO: 11) |
| mCRADD | Forward | 5-GAAGAAATGGAAGCCAGAG-3 (SEQ ID NO: 12) |
| | Reverse | 5-CTGTAGGCAGCTCGGCTG-3 (SEQ ID NO: 13) |
| hBCL10 | Forward | 5-CCCGCTCCGCCTCCTCTCCTT-3 (SEQ ID NO: 14) |
| | Reverse | 5-GGCGCTTCTTCCGGGTCCG-3 (SEQ ID NO: 15) |
| mBCL10 | Forward | 5-GAGAGCATCCACTGTCATG-3 (SEQ ID NO: 16) |
| | Reverse | 5-GGAGAAACATCTCACTTGAG-3 (SEQ ID NO: 17) |
| mTNF-α | Forward | 5-GCGACGTGGAACTGGCAGAAG-3 (SEQ ID NO: 18) |
| | Reverse | 5-GGTACAACCCATCGGCTGGCA-3 (SEQ ID NO: 19) |
| mIL-6 | Forward | 5-TTCCATCCAGTTGCCTTCTTGG-3 (SEQ ID NO: 20) |
| | Reverse | 5-CTTCATGTACTCCAGGTAG-3 (SEQ ID NO: 21) |
| mIL-1α | Forward | 5-CTCTAGAGCACCATGCTACAGAC-3 (SEQ ID NO: 22) |
| | Reverse | 5-TGGAATCCAGGGGAAACACTG-3 (SEQ ID NO: 23) |
| mβ-actin | Forward | 5-TTCTTTGCAGCTCCTTCGTTGCCG-3 (SEQ ID NO: 24) |
| | Reverse | 5-TGGATGGCTACGTACATGGCTGGG-3 (SEQ ID NO: 25) |

Cytokine/chemokine assays-Cytokines and chemokines in tissue culture media were assayed by cytometric bead array (BD Biosciences) in the Vanderbilt Flow Cytometry Core according to the manufacturer's instructions and as described previously (Lin, Q., Liu, Y., Moore, D. J., Elizer, S. K., Veach, R. A., Hawiger, J., and Ruley, H. E. (2012) Cutting Edge: The "Death" Adaptor CRADD/RAIDD Targets BCL10 and Suppresses Agonist-Induced Cytokine Expression in T Lymphocytes. *The Journal of Immunology* 188, 2493-2497). In some experiments, cells were treated with CP-CRADD or non-CP-CRADD before stimulation.

Immunofluorescence staining and Fluorescence Microscopy-LMEC or LEII cells were plated into Lab-Tek II chamber slides (Thermo Scientific) and stimulated with LPS or thrombin (Sigma) as indicated. After stimulation, cells were fixed in 4% paraformaldehyde (Electron Microscopy Sciences), then washed in PBS and permeabilized with 0.1% Triton X-100 (Invitrogen). For immunofluorescence staining, cells were blocked with 5% normal goat serum (Jackson ImmunoResearch) before overnight incubation at 4° C. with antibodies to NFκB p65/RelA (Abcam) or VE-Cadherin and p120 (Santa Cruz) followed by incubation with Alexa 488- (Invitrogen) or Cy-3-labeled (Jackson ImmunoResearch) secondary antibodies. Alexa 488-labeled phalloidin (Cytoskeleton, Inc.) was used to visualize F-actin polymerization in permeabilized cells. Slides were mounted with ProLong Gold Antifade reagent containing DAPI (Invitrogen) to stain nuclei. Images were captured with MetaMorph software on an Axioplan widefield microscope in the Vanderbilt Cell Imaging Core facility using a 40× or 63× oil immersion objective, as indicated.

Design, preparation and intracellular delivery of recombinant CRADD proteins-Design, production, and analysis of recombinant murine CRADD proteins followed previously published protocols (Fletcher, T. C., DiGiandomenico, A., and Hawiger, J. (2010) Extended anti-inflammatory action of a degradation-resistant mutant of cell-penetrating suppressor of cytokine signaling 3. *The Journal of biological chemistry* 285, 18727-18736; Jo, D., Liu, D., Yao, S., Collins, R. D., and Hawiger, J. (2005) Intracellular protein therapy with SOCS3 inhibits inflammation and apoptosis. *Nat Med* 11, 892-898). Plasmid constructs for wild type (non-CP-CRADD) and cell-penetrating (CP-CRADD) were produced using standard molecular biology techniques. CP-CRADD contains a membrane-translocating motif (MTM) that enables it to cross the plasma membrane and the $NH_2$-teminal His6 tag for affininity purification of recombinant CRADD protein and its fragments. Proteins were isolated from bacterial inclusion bodies using previously described protocols and dialyzed into DMEM supplemented with 1% pen/strep and 66 µM PEG3350. LPS content in all recombinant protein preparations was below the level of detection (0.06 EU/ml) by Limulus assay (Endosafe, Charles River), performed according to the manufacturer's instructions. To confirm intracellular delivery of CP-CRADD, human ST1.6R endothelial cells were treated for 1 hour with equimolar concentrations (10 µM) of non-CP-CRADD and CP-CRADD or medium alone. The cells were washed with warm DMEM without serum and treated with 7 µg/ml proteinase K (Sigma) for 10 min to remove proteins attached to the cell surface, followed by a wash in warm DMEM supplemented with 5% FBS. Pelleted cells were lysed in RIPA buffer supplemented with protease inhibitors (Sigma). Lysates were cleared by centrifugation then analyzed by immunoblotting using antibodies to CRADD and β-actin. While some membrane-associated non-CP-CRADD is detected by immunoblotting, CP-CRADD is 2-3 fold more abundant when recombinant proteins are normalized to endogenous CRADD or β-actin.

Endothelial cell permeability-LMEC ($1 \times 10^4$, passage 3 or 4) isolated from cradd+/+ and cradd−/− mice, or human ST1.6R cells were seeded onto 24-well Transwell insets (Costar) pre-coated with type I collagen and incubated until confluent. Confluent monolayers were serum-starved in 0.5% heat-inactivated FBS for 24 h, then left unstimulated or stimulated with vascular permeability inducers as indicated. In some experiments, cells were treated with CP-CRADD or non-CP-CRADD before stimulation. Monolayer permeability was assessed by detection of FITC-Dextran in the lower chamber at various times after addition of 1 mg/ml 10 kDa FITC-Dextran or the molar equivalent of 70 kDa FITC-Dextran (Life Technologies) to the top chamber. It was determined that the relative fluorescence of 70 kDa FITC-Dextran is approximately 6 fold greater than that of 10 kDa FITC-Dextran at equal molarities.

Statistical analyses-Data analysis and statistical calculations were performed using Prism (GraphPad). Cytokine and chemokine levels in cultured cell supernatants, and nuclear levels of p65/Rel A were compared using an unpaired t test with Welch's correction for unequal SDs. Quantification of RT-PCR bands was used to calculate the fold change in transcripts compared to non-transduced cells stimulated with LPS or thrombin and statistical differences were determined by Student's t test. For permeability experiments, the p values shown compare the area under the curve (AUC)

calculated for each condition, analyzed by an unpaired t test with Welch's correction for unequal SDs. Additional evaluation of permeability curves by repeated measures two-way analysis of variance resulted in a p value of <0.0001 for all indicated comparisons. In all experiments, a p value of <0.05 was considered significant.

Results

The outcome of inflammation depends on the balance between proinflammatory mediators and anti-inflammatory suppressors. Prior studies in immune cells (T lymphocytes) established that CRADD inhibits pro-inflammatory signaling at the level of BCL10-dependent NFκB activation (Lin, Q., Liu, Y., Moore, D. J., Elizer, S. K., Veach, R. A., Hawiger, J., and Ruley, H. E. (2012) Cutting Edge: The "Death" Adaptor CRADD/RAIDD Targets BCL10 and Suppresses Agonist-Induced Cytokine Expression in T Lymphocytes. *The Journal of Immunology* 188, 2493-2497; Paul, S., and Schaefer, B. C. (2013) A new look at T cell receptor signaling to nuclear factor-kappaB. *Trends in immunology* 34, 269-281). The possibility of a similar function for CRADD in non-immune cells (endothelial cells) in which BCL10 plays a pivotal role in the CARMA3 signalosome-dependent activation of the NFκB pathway was investigated.

Expression of CRADD in endothelial cells—It was hypothesized that CRADD could negatively regulate BCL10, an essential component of the CARMA3 signalosome assembled in endothelial cells following their response to proinflammatory stimuli. To test this hypothesis, expression of CRADD mRNA and protein in primary human endothelial cells (HUVEC), primary murine LMEC, and human and murine endothelial cell lines was first examined. It was shown by RT-PCR (FIG. 1A) and immunoblot analysis (FIG. 1B) that HUVEC, LMEC and endothelial cell lines constitutively express CRADD. This study was extended to epithelial cells, which also express CRADD (unpublished observation) along with known expression of BCL10 in human intestinal epithelial cells (S. Bhattacharyya et al *Am. J. Physiol Gastrointest Liver Physiol*, 2007, 293: G429-G437; S. Bhattacharyya et al *J Biol Chem* 2008, 283: 10550-10558).

The anti-inflammatory action of CRADD is dependent on BCL10-BCL10 was previously identified as a direct target of CRADD responsible for suppression of T cell receptor agonist-evoked signaling in T lymphocytes (Lin, Q., Liu, Y., Moore, D. J., Elizer, S. K., Veach, R. A., Hawiger, J., and Ruley, H. E. (2012) Cutting Edge: The "Death" Adaptor CRADD/RAIDD Targets BCL10 and Suppresses Agonist-Induced Cytokine Expression in T Lymphocytes. *The Journal of Immunology* 188, 2493-2497). This new function of CRADD is dependent on its CARD domain, which binds to BCL10 and impedes its interaction with CARMA1 (Lin, Q., Liu, Y., Moore, D. J., Elizer, S. K., Veach, R. A., Hawiger, J., and Ruley, H. E. (2012) Cutting Edge: The "Death" Adaptor CRADD/RAIDD Targets BCL10 and Suppresses Agonist-Induced Cytokine Expression in T Lymphocytes. *The Journal of Immunology* 188, 2493-2497). Thus, the CRADD-BCL10 axis prevents formation of a complete CARMA1 signalosome required for activation of the NFκB signaling pathway in immune cells (Lin, Q., Liu, Y., Moore, D. J., Elizer, S. K., Veach, R. A., Hawiger, J., and Ruley, H. E. (2012) Cutting Edge: The "Death" Adaptor CRADD/RAIDD Targets BCL10 and Suppresses Agonist-Induced Cytokine Expression in T Lymphocytes. *The Journal of Immunology* 188, 2493-2497). BCL10 is expressed in endothelial cells (FIG. 1C), consistent with other reports that also documented expression of CARMA3 and MALT1. BCL10 has been identified as an important mediator of NFκB activation, and is recruited to Toll-like receptor 4 (TLR4) signaling complexes in response to LPS stimulation by interacting with IRAK-1. This interaction was confirmed in LPS-stimulated LMEC from cradd+/+ mice and human lung microvascular endothelial HPMEC-ST1.6R cells by showing stimulus- and time-dependent association of BCL10 with IRAK-1 (FIG. 1D). HPMEC-ST1.6R cells were chosen because they display the major constitutive and inducible endothelial cell characteristics and show an angiogenic response on Matrigel similar to that of primary human endothelial cells isolated from umbilical vein (HUVEC), lung (HPMEC), and skin (HDMEC).

Figure 3B:
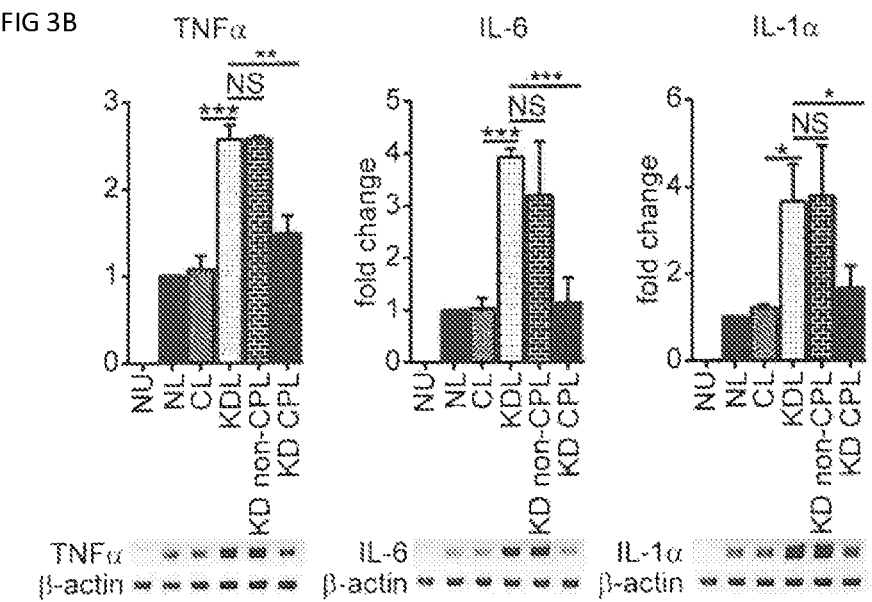
Figure 3C:
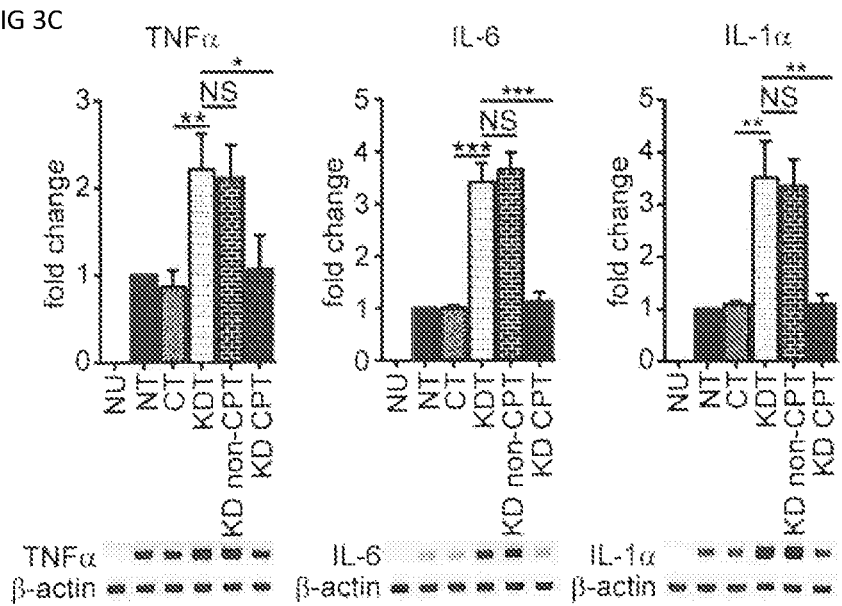

Subsequently, it was demonstrated that the regulatory action of CRADD depends on BCL10 in stimulated endothelial cells by employing shRNA knockdown of CRADD and/or BCL10 (FIGS. 2A and B). Upon stimulation with the TLR4 agonist LPS, or the proteinase-activated receptor 1 (PAR-1) agonist thrombin, CRADD K/D LEII cells display significantly increased transcripts for cytokines TNF-α, IL-6, and IL-1a (FIG. 3). Consistent with increased expression of IL-6 mRNA transcripts, IL-6 protein expression was also increased in response to LPS and thrombin (FIGS. 2 C and D, right). Thus, endothelial production of this pleotropic cytokine and permeability inducer is negatively controlled by CRADD, regulating signaling pathways evoked by two distinct agonists, LPS and thrombin, in endothelial cells. While CRADD K/D cells produced more IL-6 in response to LPS or thrombin, BCL10 K/D endothelial cells displayed the opposite effect (FIGS. 2C and D, left). Simultaneous reduction in CRADD and BCL10 expression (CRADD/BCL10 K/D) abrogated the increased IL-6 expression observed in CRADD-deficient cells stimulated with LPS and thrombin (FIGS. 2C and D, right). Thus, increased IL-6 expression in CRADD-depleted cells depends on BCL10. This enhancement of LPS-induced signaling to the nucleus in CRADD K/D LEII cells resulted in predicted downstream activation events as demonstrated by elevated levels of nuclear NFκB RelA/p65 (p65) in LPS-stimulated CRADD K/D cells compared to LPS-stimulated control cells (FIG. 2E).

Figure 4A:
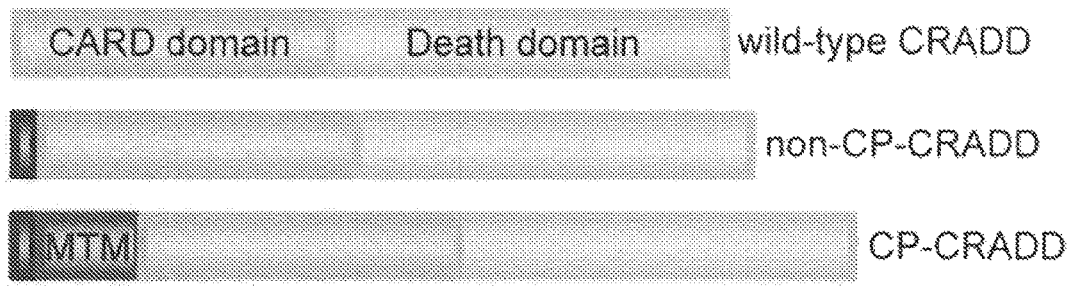
FIGS. 4A, 4B, and 4C show design, purity and intracellular delivery of recombinant CP-CRADD.
Figure 4B:
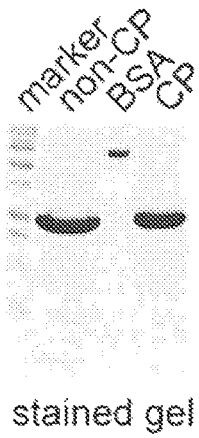
Figure 4C:
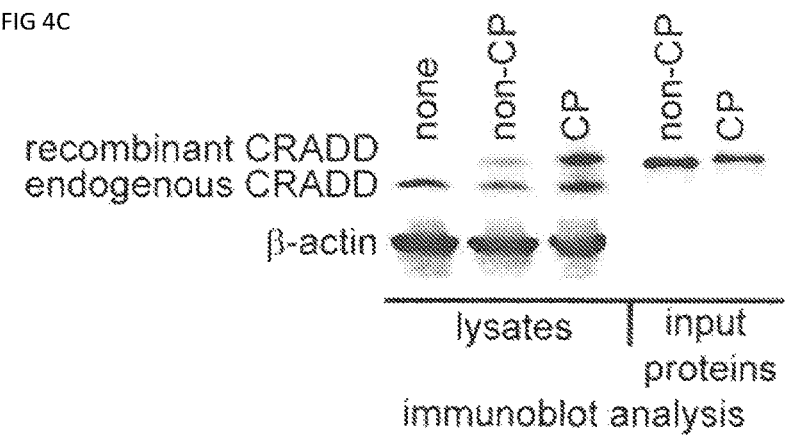

Proinflammatory agonist-induced cytokine expression is suppressed by replenishing endogenous CRADD with a novel recombinant cell-penetrating (CP) protein, CP-CRADD—it was reasoned that by increasing intracellular content of CRADD in endothelial cells one can attenuate their responses to proinflammatory agonists. Consistent with prior evidence with recombinant cell-penetrating SOCS1 and SOCS3 that inhibited inflammation and apoptosis (Fletcher, T. C., DiGiandomenico, A., and Hawiger, J. (2010) Extended anti-inflammatory action of a degradation-resistant mutant of cell-penetrating suppressor of cytokine signaling 3. *The Journal of biological chemistry* 285, 18727-18736; Jo, D., Liu, D., Yao, S., Collins, R. D., and Hawiger, J. (2005) Intracellular protein therapy with SOCS3 inhibits inflammation and apoptosis. *Nat Med* 11, 892-898; DiGiandomenico, A., Wylezinski, L. S., and Hawiger, J. (2009) Intracellular delivery of a cell-penetrating SOCS1 that targets IFN-gamma signaling. *Science signaling* 2, ra37), a novel recombinant CP-CRADD protein (FIG. 4A) was developed to restore CRADD protein in CRADD-deficient endothelial cells and its regulatory function was analyzed. Purity and yields of the recombinant CRADD protein homologs were comparable (FIG. 4B). Intracellular delivery of CP-CRADD was verified in human and murine endothelial cells by immunoblot analysis (FIG. 4C) before use in functional assays, which ultimately provided proof of CP-CRADD intracellular activity.

Figure 5A:
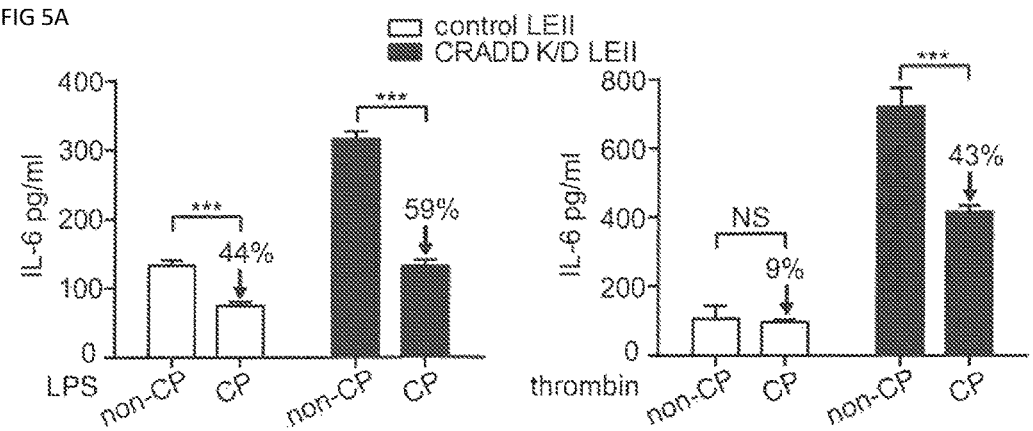
FIGS. 5A, 5B, 5C, and 5D show intracellular delivery of CP-CRADD suppresses agonist-induced IL-6 and MCP-1 expression in wild-type and CRADD-deficient endothelial cells.

As corollary evidence of the negative regulatory function of CRADD in endothelial cells, CP-CRADD protein delivery to CRADD-depleted LEII cells (CRADD K/D) significantly suppressed both LPS- and thrombin-induced IL-6 expression (FIG. 5A). Consistent with the changes in protein expression, increased mRNA transcripts for TNF-α, IL-6 and IL-1a in CRADD K/D cells were reduced by treatment with CP-CRADD to the levels displayed by CRADD-sufficient LEII cells after stimulation with LPS or thrombin (see FIGS. 3B and C). Moreover, treatment with CP-CRADD significantly reduced IL-6 protein in CRADD-sufficient LEII control cells stimulated with LPS, though a similar reduction in IL-6 induced by thrombin in the control LEII cells was not apparent (FIG. 5A).

Figure 5B:
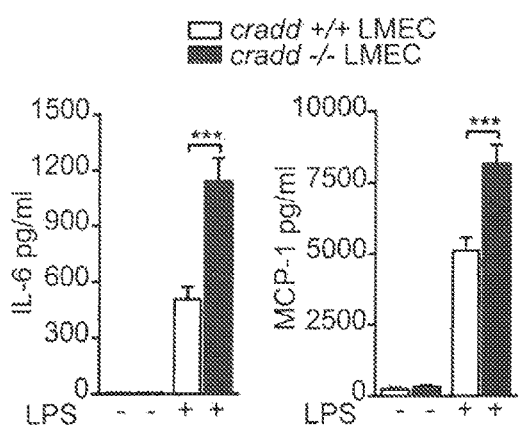
Figure 5C:
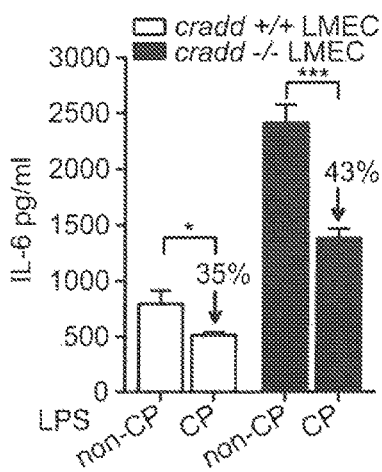
Figure 5D:
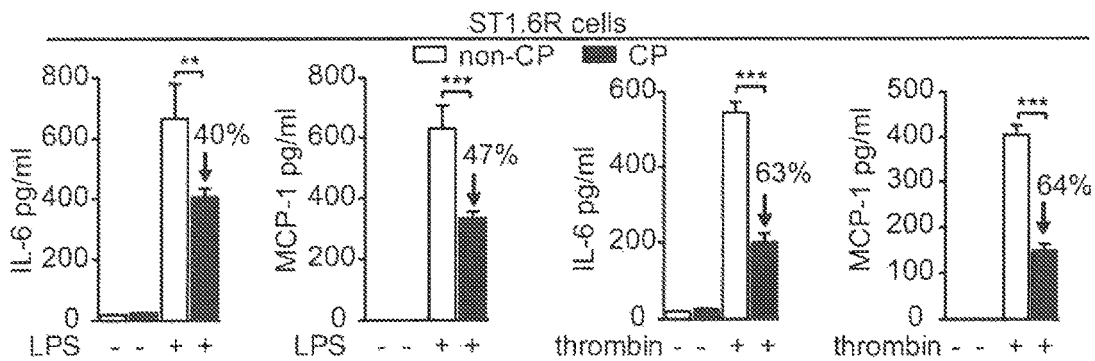

The inflammatory response to LPS in LMEC derived from previously characterized cradd−/− and wild-type cradd+/+ control mice was next compared. As shown in FIG. 1B, LMEC isolated from cradd−/− mice are deficient in CRADD protein while LMEC from wild-type cradd+/+ mice contain endogenous CRADD. Concordant with results obtained in LEII cells, primary LMEC isolated from cradd−/− mice also displayed an enhanced response to LPS stimulation compared to LMEC from wild-type cradd+/+ mice (FIG. 5B). Treatment with CP-CRADD suppressed IL-6 production of LMEC from cradd−/− mice by 43%, and, significantly, in LMEC from cradd+/+ mice, CP-CRADD supplemented endogenous CRADD to reduce their IL-6 production in response to LPS by 35%, (FIG. 5C). This beneficial effect of CRADD augmentation was further explored in the human lung microvascular endothelial cell line HPMEC-ST1.6R. The enhanced production of IL-6 and monocyte chemoattractant protein-1 (MCP-1/CCL2) in response to LPS was counteracted by treatment with CP-CRADD, reducing their expression by 40% and 47%, respectively (FIG. 5D). Additionally, thrombin-induced IL-6 and MCP-1 were reduced by 63% and 64% respectively. The chemokine MCP-1 is known to induce reorganization of tight junctions proteins and increase endothelial permeability. Thus, intracellular delivery of recombinant CP-CRADD complemented the negative regulation of cytokine/chemokine expression by endogenous CRADD. The contrast between the results from ST1.6R cells and control LEII cells (FIG. 5A) may be attributed to low expression of IL-6 by LEII cells in response to thrombin.

Figure 6A:
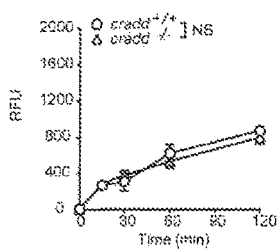
FIGS. 6A, 6B, 6C, 6D, 6E, 6F, 6G, 6H, and 6I show endothelial permeability of CRADD-deficient primary murine LMEC and CRADD-sufficient human ST1.6R endothelial monolayers is regulated by CP-CRADD.
Figure 6B:
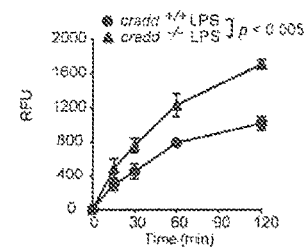
Figure 6C:
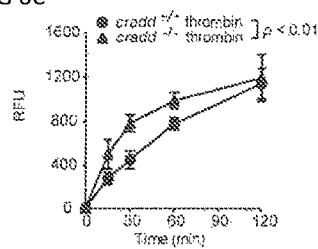
Figure 6D:
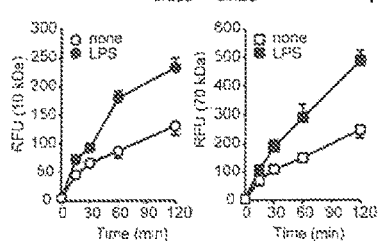
Figure 6E:
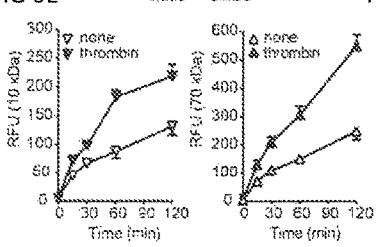
Figure 6F:
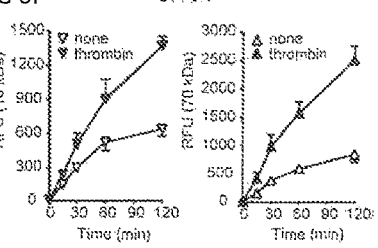
Figure 6G:
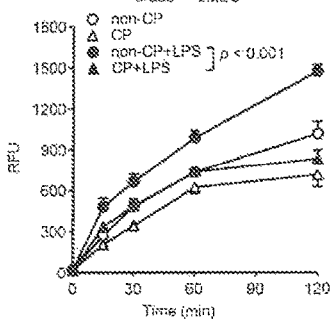
Figure 6H:
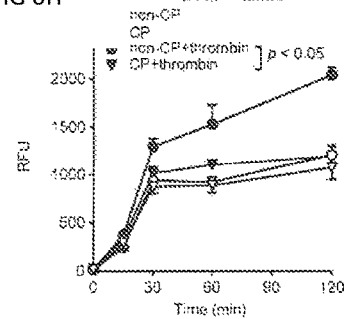
Figure 6I:
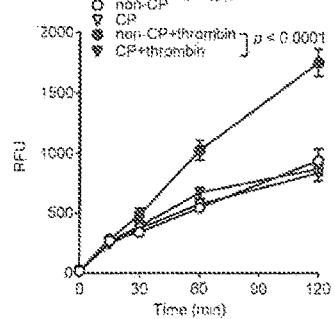

Finally, agonist-induced endothelial monolayer permeability, a hallmark of inflammation, is enhanced in CRADD-deficient endothelial cells. Therefore—the role of CRADD in maintaining endothelial barrier function was analyzed by first comparing permeability of LMEC monolayers from cradd+/+ and cradd−/− mice. This assay was based on monitoring the passage of FITC-labeled Dextran through the monolayer. In the absence of stimulation, there was no difference in permeability between monolayers from cradd−/− and cradd+/+ LMEC (FIG. 6A). The barrier function of primary LMEC was then tested in agonist-induced permeability assays. Proinflammatory agonists LPS and thrombin induced significantly increased permeability in cradd−/− LMEC monolayers as compared to cradd+/+ LMEC monolayers (FIGS. 6B and C). Notably, agonist-induced permeability of endothelial monolayers to both small and large tracers (10 kDa FITC-Dextran and 70 kDa FITC-Dextran, respectively) was similar (FIG. 6D-F). CP-CRADD treatment restored barrier function to cradd−/− LMEC (FIGS. 6G and H) stimulated with either LPS or thrombin, providing definitive proof of the negative regulatory function of CRADD in endothelial cells. Moreover, in CRADD-sufficient human ST1.6R cell monolayers, thrombin-induced permeability was reduced by supplementation with CP-CRADD (FIG. 6I), suggesting that supplementation of endogenous CRADD with CP-CRADD may stabilize endothelial barrier function during protracted inflammatory signaling.

F-Actin polymerization and adherens junctions are altered in CRADD-deficient cells-Stimulation of endothelial cell monolayers with agonists triggers morphological changes through reorganization of the actin cytoskeleton, leading to increased permeability. The mechanism of increased agonist-induced permeability in CRADD-deficient endothelial monolayers was explored by investigating changes in F-actin organization (FIG. 7) and the adherens junction protein VE-cadherin and its adaptor p120 (FIG. 8) in cradd+/+ and cradd−/− LMEC stimulated with the permeability inducers LPS or thrombin.

Unstimulated LMEC from both cradd+/+ and cradd−/− mice stained with fluorescent phalloidin exhibited an actin cytoskeleton with thin F-actin fibers sparsely crossing the body of cells (FIGS. 7A and B). LPS and thrombin stimulation induced changes in F-actin organization (FIG. 7C-F), displaying a strong pattern of polymerized actin with prominently thick F-actin fiber bundles. However, loss of peripheral F-actin and more prominent retraction of the cell mass toward the center were evident in cradd−/− LMEC, leading to increased gaps in the monolayer (indicated by arrows) (FIGS. 7D and F).

Immunostaining for the adherens junction protein VE-cadherin and its adaptor p120 produced a strong signal, which appeared as a contiguous line of varied thickness along cell borders in quiescent endothelial cells (FIGS. 8A and B). Note that unstimulated cradd−/− endothelial cells displayed a spindle-like shape rather than the typical cobblestone pattern of cradd+/+ endothelial cells. LPS and thrombin stimulation triggered a striking distortion of the VE-cadherin/p120 contiguous border pattern with a visible reduction of VE-cadherin/p120 peripheral staining (FIG. 8C-F). Stimulated cradd−/− LMEC displayed a more dramatic disturbance in the border pattern compared to cradd+/+ LMEC, evidenced by areas of deficient staining surrounding the gaps formed in the initially integral monolayer (indicated by arrows) (FIGS. 8D and F). These results indicate that BCL10-mediated F-actin disorganization and adherens junction disruption are controlled by CRADD.

Herein it is shown that the intracellular adaptor CRADD is expressed in non-immune cells. In primary human and murine endothelial cells, CRADD is involved in maintaining their integrity by acting as a negative regulator of the inflammatory response. This physiologic action of CRADD is dependent on its interaction with BCL10, a key component of the CARMA3 signalosome in microvascular endothelial cells. This anti-inflammatory function of CRADD in endothelial cells is consistent with its role as a negative regulator of the BCL10-containing CARMA1 signalosome in immune cells, as documented in an earlier study of CRADD (Lin, Q., Liu, Y., Moore, D. J., Elizer, S. K., Veach, R. A., Hawiger, J., and Ruley, H. E. (2012) Cutting Edge: The "Death" Adaptor CRADD/RAIDD Targets BCL10 and Suppresses Agonist-Induced Cytokine Expression in T Lymphocytes. *The Journal of Immunology* 188, 2493-2497). BCL10 interacts not only with CARMA1, which is restricted to cells of the immune system, but also with its close homolog, CARMA3, which has a much broader expression pattern including endothelial and epithelial cells. Therefore, expression of CRADD in endothelial and other cell types, e.g. epithelial cells, follows that of BCL10 and may also provide an anti-inflammatory CRADD-BCL10 axis in those cells. CRADD is also expressed in human brain microvascular endothelial cells, the mainstays of blood-brain barrier. CRADD expression and function in human brain microvascular endothelial cells that are part of the neurovascular unit comprising also astrocytes and neurons provides another target for anti-inflammatory and cytoprotective action of CP-CRADD. CRADD interaction with BCL10 transcends its engagement in the CARMA3 signalosome as BCL10 is known to interact with IRAK-1. CRADD negatively regulates LPS-triggered signaling to the nucleus mediated by NFκB (see FIG. 2E), a process that depends on TLR4-evoked activation of IRAK-1 that binds BCL10. Hence CRADD targeting of BCL10 may reduce the outcome of LPS action on endothelial cells. LPS is a very potent proinflammatory virulence factor of Gram-negative bacteria, the cause of sepsis in two-thirds of patients that also suffer acute brain dysfunction and severe cognitive impairment (Hawiger, J., Veach R A, and Zienkiewicz J. new paradigms in sepsis: from prevention to protection of failing microcirculation. J. Thromb. Haemost. 2015, 13:1-14). As mutations of the gene encoding CRADD protein are linked to Mental Retardation, autosomal recessive 34 (MRT 34) with significantly impaired cognitive function, intracellular protein therapy with CP-CRADD opens up a new approach to these intractable disorders.

The results based on co-IP analysis (FIG. 1D) and BCL10 silencing (FIG. 2), demonstrate BCL10 involvement in the LPS/TLR4 signaling pathway. This pathway is negatively regulated by CRADD and its novel recombinant cell-penetrating homolog CP-CRADD.

Thrombin/PAR-1 signaling to mobilize NFκB for nuclear translocation depends on initial protein kinase C activation, with subsequent steps mediated by BCL10 to engage the canonical NFκB machinery and shift endothelial function toward an "activated" phenotype. As shown herein, thrombin dramatically increased cytokine and chemokine production and significantly induced permeability of the endothelial monolayer. The CARMA3 signalosome links PAR-1-evoked signaling to activation of the IκB kinase signaling complex assembled around TRAF6 through ubiquitination of NFκB essential modulator (NEMO/IKKγ), the regulatory subunit of the IκB kinase complex. In immune cells, BCL10 activates the NFκB pathway through NEMO. Though there are significant differences in how the CARMA1 and CARMA3 signalosomes communicate with PAR-1 and other receptors, such as the choice of 3-phosphoinositide-dependent protein kinase 1 and β-arrestin 2, the CARMA3 signalosome shares its positive regulator BCL10 with the CARMA1 signalosome found in lymphocytes. Hence BCL10 presents itself as an easy target for CRADD negative regulation of both CARMA 1 and CARMA3 signalosomes in agonist-stimulated immune and non-immune cells, respectively.

BCL10 has emerged as a key positive mediator of inflammatory signals, as it has been reported to interact with other CARD domain-containing proteins, including CARD 9, 10, 11 and 14, which are thought to function as upstream regulators in NFκB signaling. Independent of NFκB signaling, BCL10 is also linked to remodeling of F-actin, which is connected to transmembrane junctional proteins that control the barrier function of endothelial cells (Rueda, D., Gaide, O., Ho, L., Lewkowicz, E., Niedergang, F., Hailfinger, S., Rebeaud, F., Guzzardi, M., Conne, B., Thelen, M., Delon, J., Ferch, U., Mak, T. W., Ruland, J., Schwaller, J., and Thome, M. (2007) Bcl10 controls TCR- and FcgammaR-induced actin polymerization. J Immunol 1178, 4373-4384). As the non-immune mainstays of the blood-tissue barrier, endothelial cells are connected by highly regulated tight and adherens junctions, which control paracellular leakage of plasma fluid and proteins that contribute to increased endothelial permeability. LPS induces F-actin remodeling through activation of a Src family kinase and TNF receptor associated factor 6 (TRAF6). As shown in FIG. 7, CRADD-deficient cells demonstrate an altered pattern of F-actin polymerization in response to LPS and thrombin stimulation compared to CRADD-sufficient cells. Therefore, CRADD, by targeting BCL10, plays an important role in the negative regulation of BCL10-mediated F-actin polymerization. CRADD deficiency thereby increases inducible but not constitutive permeability of endothelial monolayers compared to CRADD-sufficient endothelium.

Proinflammatory agonist-induced stress fiber formation overlaps with redistributed VE cadherin, an endothelium-specific member of the cadherin family of adhesion proteins found in adherens junctions. Inside the cell, VE-cadherin interacts with its adaptor p120. As shown in FIG. 8, the VE-cadherin/p120 system was highly perturbed in CRADD-deficient cells upon their stimulation with proinflammatory agonists. Thus, the evidence presented here points to another important role for endothelial CRADD as an inducible physiologic regulator of vascular permeability, a cardinal sign of inflammation.

This study shows significantly increased IL-6 and MCP-1 expression by CRADD-deficient endothelial cells in response to LPS and thrombin, suggesting that depletion of endogenous CRADD by inflammatory signaling may contribute to the enhanced action of IL-6 and MCP-1 as endothelial permeability inducers. It was shown herein that the changes induced by inflammatory signaling are sufficient to allow permeability to large molecules (FIG. 6 D-F), such as plasma proteins. In turn, reduction of BCL10-mediated inflammatory signaling by a novel recombinant protein, CP-CRADD, offers a new strategy to control vascular inflammatory responses not only in non-immune cells (endothelial cells) as demonstrated in this study but also in immune cells. CRADD is also expressed in human brain microvascular endothelial cells, suggesting its potential anti-inflammatory and cytoprotective function there as well. In addition, CP-CRADD can be used to quell inflammation-mediated injury of epithelial cells in respiratory, gastrointestinal, and renal systems.

In summary, this study provides new evidence that CRADD plays a pivotal role in maintaining the integrity of endothelial monolayers. The compositions and methods described herein provide for the development of a novel treatment for inflammatory vascular disorders.

Other Embodiments

Any improvement may be made in part or all of the compositions, kits, and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A composition comprising a pharmaceutically acceptable carrier and a cell-penetrating caspase and receptor interacting protein adaptor with death domain (CP-CRADD) in an amount sufficient to reduce or block BCL10 expression or activity, reduce BCL-10-mediated inflammation, and/or treat BCL-10-mediated inflammation with a condition in a subject; wherein the death domain of CP-CRADD is deleted.

2. The composition of claim 1, wherein the amount is sufficient to reduce production of IL-6, monocyte chemoattactant protein 1 or other cytokines and chemokines produced by endothelial cell, smooth muscle cells, and/or epithelial cells.

3. The composition of claim 2, wherein the CP-CRADD comprises a membrane translocating motif (MTM) having the sequence AAVLLPVLLAAP (SEQ ID NO:1).

4. A device impregnated with the composition of claim 1.

5. The device of claim 4, wherein the device is a stent, scaffold, matrix, or inhaler.

6. The composition of claim 1, wherein the condition comprises hypertension, atherosclerosis, aortic aneurysm formation, neurovascular lesions, epithelial injury in respiratory, gastrointestinal, hepatobiliary, and genitourinary systems.

7. A method of treating BCL10-mediated inflammation in a mammalian subject comprising administering the composition of claim 1 to the mammalian subject in an amount effective for blocking or reducing BCL10 expression or activity thereby reducing or blocking BCL10-mediated inflammation and/or treating a condition associated pith BCL10-mediated inflammation with a condition in the mammalian subject.

8. The method of claim 7, wherein administration of the composition inhibits proinflammatory signaling in at least one of: endothelial cells, vascular smooth muscle calls, epithelial cells, lymphocytes and leukocytes in the subject.

9. The method of claim 7, wherein the subject is a human.

10. The method of claim 7, wherein the CP-CRADD comprises an MTM having the sequence AAVLLPVLLAAP (SEQ ID NO:1).

11. The method of claim 7, wherein the CP-CRADD lacks its CARD domain.

12. The method of claim 7, wherein CP-CRADD comprises an MTM having the sequence AAVALLPAVLLALLAP (SEQ ID NO:2).

13. The method of claim 7, wherein CP-CRADD comprises an MTM having the sequence VTVLALGALAGVGVG (SEQ ID NO:3).

\* \* \* \* \*

UNITED STATES PATENT AND TRADEMARK OFFICE
CERTIFICATE OF CORRECTION

PATENT NO. : 11,026,992 B2  
APPLICATION NO. : 16/448960  
DATED : June 8, 2021  
INVENTOR(S) : Jack J. Hawiger et al.

Page 1 of 1

It is certified that error appears in the above-identified patent and that said Letters Patent is hereby corrected as shown below:

In the Claims

Column 36, Line 54-56 for Claim reference numeral '7', "inflammation and/or treating a condition associated with BCL10-mediated inflammation in the mammalian subject." should read
-- "inflammation and/or BCL10-mediated inflammation with a condition in the mammalian subject." --

Signed and Sealed this  
Seventh Day of December, 2021

Drew Hirshfeld  
*Performing the Functions and Duties of the*  
*Under Secretary of Commerce for Intellectual Property and*  
*Director of the United States Patent and Trademark Office*